US010231820B2

(12) United States Patent
Vacanti et al.

(10) Patent No.: US 10,231,820 B2
(45) Date of Patent: *Mar. 19, 2019

(54) FABRICATION OF VASCULARIZED TISSUE USING MICROFABRICATED TWO-DIMENSIONAL MOLDS

(71) Applicants: The Charles Stark Draper Laboratory, Inc., Cambridge, MA (US); The General Hospital Corporation, Boston, MA (US)

(72) Inventors: Joseph P. Vacanti, Boston, MA (US); Young-Moon M. Shin, Somerville, MA (US); Jennifer Ogilvie, San Francisco, CA (US); Alexander Sevy, Houston, TX (US); Tomoyuki Maemura, Boston, MA (US); Osamu Ishii, Arlington, MA (US); Mohammad R. Kaazempur-Mofrad, Cambridge, MA (US); Jeffrey T. Borenstein, Holliston, MA (US); Kevin R. King, Western Springs, IL (US); Chiao-Chun Wang, Baltimore, MD (US); Eli Weinberg, Needham, MA (US)

(73) Assignees: The Charles Stark Draper Laboratory, Inc., Cambridge, MA (US); The General Hospital Corporation, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/354,865

(22) Filed: Nov. 17, 2016

(65) Prior Publication Data
US 2017/0296322 A1  Oct. 19, 2017

Related U.S. Application Data

(60) Continuation of application No. 14/153,591, filed on Jan. 13, 2014, now Pat. No. 9,738,860, which is a continuation of application No. 12/785,865, filed on May 24, 2010, now Pat. No. 8,642,336, which is a division of application No. 10/187,247, filed on Jun. 28, 2002, now Pat. No. 7,759,113.

(60) Provisional application No. 60/367,675, filed on Mar. 25, 2002.

(51) Int. Cl.
| A61F 2/06 | (2013.01) |
| C12M 1/00 | (2006.01) |
| C12N 5/00 | (2006.01) |
| A61L 27/38 | (2006.01) |
| A61L 27/36 | (2006.01) |
| C12N 5/071 | (2010.01) |
| C12M 3/00 | (2006.01) |
| C12M 1/12 | (2006.01) |
| A61L 27/58 | (2006.01) |
| B33Y 80/00 | (2015.01) |

(52) U.S. Cl.
CPC .......... *A61F 2/062* (2013.01); *A61L 27/3604* (2013.01); *A61L 27/3804* (2013.01); *A61L 27/3808* (2013.01); *A61L 27/3891* (2013.01); *A61L 27/3895* (2013.01); *A61L 27/58* (2013.01); *C12M 21/08* (2013.01); *C12M 23/06* (2013.01); *C12M 23/30* (2013.01); *C12M 25/02* (2013.01); *C12N 5/0062* (2013.01); *C12N 5/0697* (2013.01); *A61F 2240/004* (2013.01); *A61F 2240/005* (2013.01); *A61L 2300/64* (2013.01); *B33Y 80/00* (2014.12); *C12N 2533/12* (2013.01); *C12N 2533/30* (2013.01); *Y10T 29/49826* (2015.01)

(58) Field of Classification Search
None
See application file for complete search history.

(56) References Cited

U.S. PATENT DOCUMENTS

| 3,907,687 | A  * | 9/1975 | Hoeltzenbein | B01D 61/28 210/321.75 |
| 7,670,797 | B2 * | 3/2010 | Vacanti | C12Q 1/00 435/30 |
| 7,759,113 | B2 * | 7/2010 | Vacanti | A61L 27/3604 424/422 |
| 7,776,021 | B2 * | 8/2010 | Borenstein | A61M 1/1678 435/2 |
| 8,173,361 | B2 * | 5/2012 | Vacanti | C12Q 1/00 435/4 |
| 8,491,561 | B2 * | 7/2013 | Borenstein | A61M 1/1678 435/2 |
| 8,642,336 | B2 * | 2/2014 | Vacanti | A61L 27/3604 435/1.1 |

* cited by examiner

*Primary Examiner* — Allison M Fox
(74) *Attorney, Agent, or Firm* — Burns & Levinson LLP; George N. Chaclas

(57) ABSTRACT

Methods and materials for making complex, living, vascularized tissues for organ and tissue replacement, especially complex and/or thick, structures, such as liver tissue is provided. Tissue lamina is made in a system comprising an apparatus having (a) a first mold or polymer scaffold, a semi-permeable membrane, and a second mold or polymer scaffold, wherein the semi-permeable membrane is disposed between the first and second molds or polymer scaffolds, wherein the first and second molds or polymer scaffolds have means defining microchannels positioned toward the semi-permeable membrane, wherein the first and second molds or polymer scaffolds are fastened together; and (b) animal cells. Methods for producing complex, three-dimensional tissues or organs from tissue lamina are also provided.

19 Claims, 31 Drawing Sheets

FIG. 3
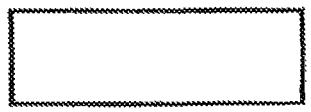
1. Start Silicon Wafer
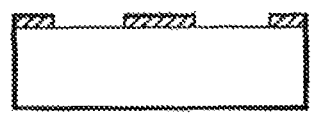
2. Pattern Photoresist
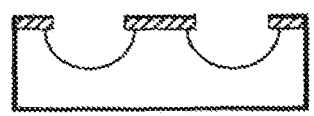
3. Isotropic Plasma Etch Silicon
4. Remove Photoresist FIG. 5
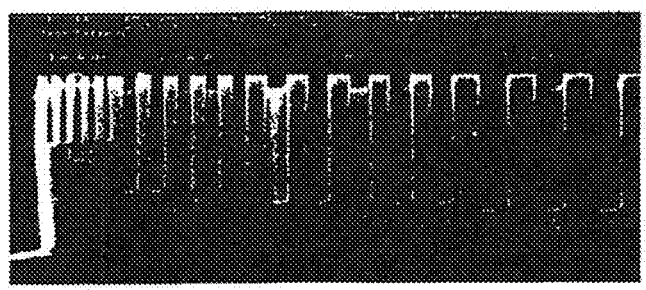
FIG. 6
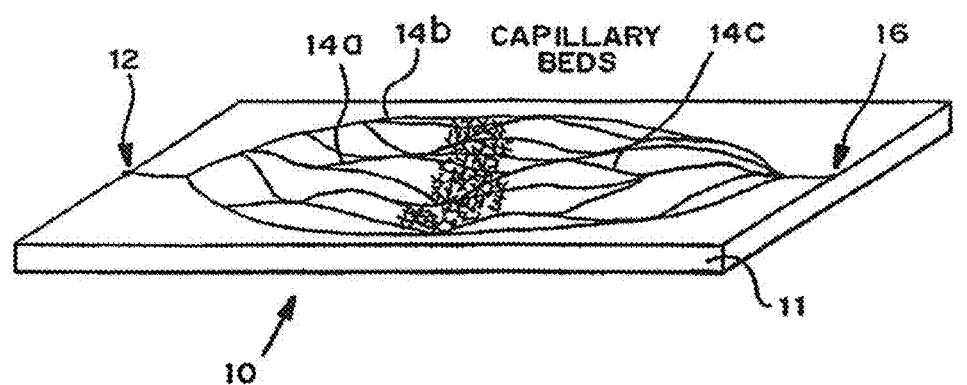
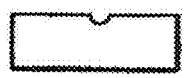
FIG. 7A
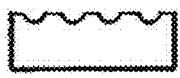
FIG. 7B
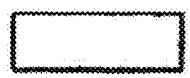
FIG. 7C

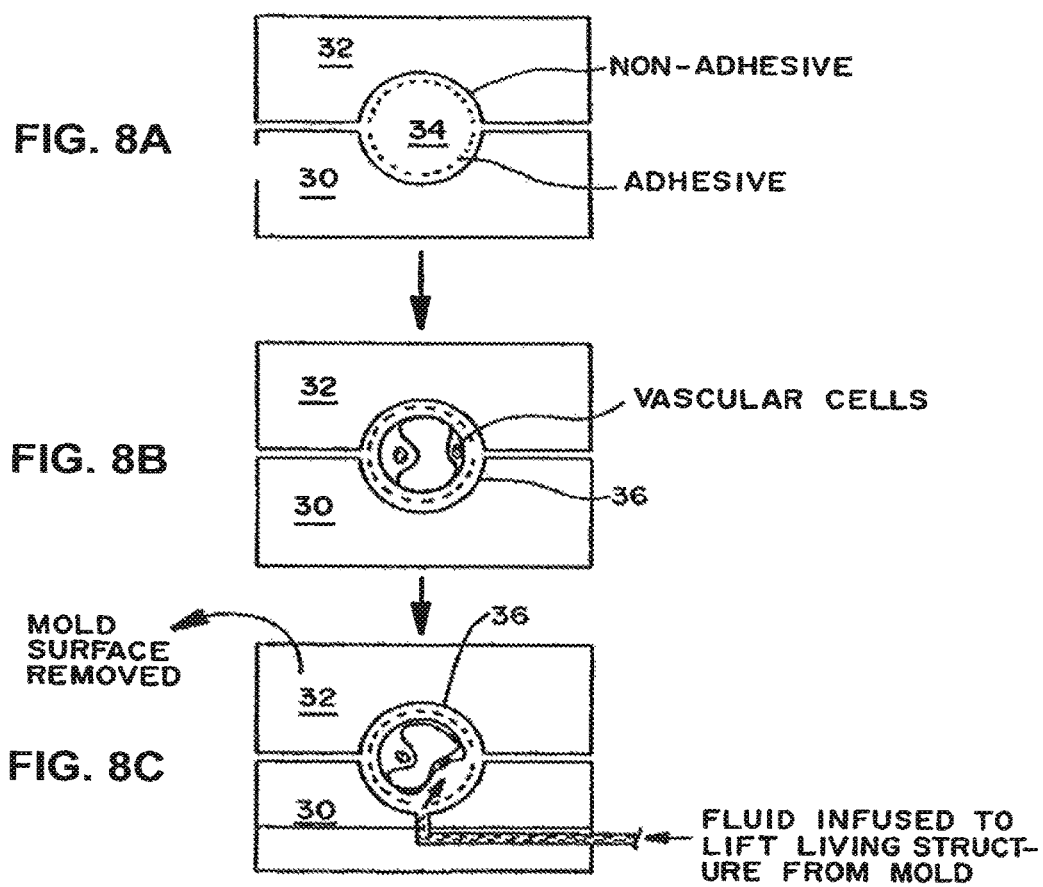

FIG. 12A  FIG. 12B 
FIG. 12C  FIG. 12D  FIG. 12E 
FIG. 12F  
FIG. 12G

ALBUMIN PRODUCTION

Proximal Tubule Cells in PDMS Device Day 6

FABRICATION OF VASCULARIZED TISSUE USING MICROFABRICATED TWO-DIMENSIONAL MOLDS

RELATED APPLICATIONS

This application is a continuation of U.S. Ser. No. 14/153,591, filed Jan. 13, 2014, which is a continuation of U.S. Ser. No. 12/785,865, filed May 24, 2010, now U.S. Pat. No. 8,642,336 which was a divisional of U.S. Ser. No. 10/187,247, filed Jun. 28, 2002, now U.S. Pat. No. 7,759,113. This application also claims the benefit of U.S. Ser. No. 60/367,675, filed Mar. 25, 2002.

STATEMENT OF POTENTIAL GOVERNMENT INTEREST

This invention was made with Government support under Grant Number HL6042404 awarded by the National Institutes of Health as well as DAMD17-99-2-9001 and DAMD17-02-0006 from the Department of the Army. The Government has certain rights in this invention.

Each of the foregoing applications and patents and articles, and each document cited or referenced in each of the foregoing applications and patents and articles, including during the prosecution of each of the foregoing applications and patents ("application and article cited documents"), and any manufacturer's instructions or catalogues for any products cited or mentioned in each of the foregoing applications and patents and articles and in any of the application and article cited documents, are hereby incorporated herein by reference. Furthermore, all documents cited in this text, and all documents cited or referenced in documents cited in this text, and any manufacturer's instructions or catalogues for any products cited or mentioned in this text or in any document hereby incorporated into this text, are hereby incorporated herein by reference. Documents incorporated by reference into this text or any teachings therein can be used in the practice of this invention. Documents incorporated by reference into this text are not admitted to be prior art. Furthermore, authors or inventors on documents incorporated by reference into this text are not to be considered to be "another" or "others" as to the present inventive entity and vice versa, especially where one or more authors or inventors on documents incorporated by reference into this text are an inventor or inventors named in the present inventive entity.

FIELD OF THE INVENTION

The present invention generally relates to the fields of organ transplantation and reconstructive surgery, and to the new field of tissue engineering. It more specifically is a new method and materials for generating tissues requiring a blood vessel supply and other complex components such as a nerve supply, drainage system and/or lymphatic system.

BACKGROUND

Vital organ failure is one of the most critical problems facing the health care field today. Organ transplantation, as currently practiced, has become a major lifesaving therapy for patients afflicted with diseases that destroy vital organs including the heart, liver, lungs, kidney and intestine. However, the shortage of organs needed for transplantation has become critical and continues to worsen. For example, in the United States, the number of patients awaiting an organ for transplant has risen above 75,000. Despite advances in living donor organ transplantation, a severe shortage of donor organs available to these patients remains as the crux of the problem. Likewise, every major field of reconstructive surgery reaches the same barrier of tissue shortage. Orthopedic surgery, vascular surgery, cardiac surgery, general surgery, neurosurgery, and the others all share this fundamental problem. Therefore, countless patients suffer as a result. Mechanical devices provide one approach to addressing the organ and tissue shortage. Xenografts provide another approach. However, due to the intrinsic limitations of these technologies, these approaches are only partial solutions to the problem.

Over the last several years, the new field of tissue engineering has arisen to meet this need. The field brings the expertise of physicians, life scientists and engineers together to solve problems of generating new tissues for transplantation and surgical reconstruction. Tissue engineering can be a complete and permanent solution to the problem of organ loss or failure, but the primary challenge for tissue engineering vital organs is the requirement for a vascular supply for nutrient and metabolite transfer. The initial approaches to this problem were described in the 1980's. Yannas, et al., Science 221, 1052 (1981) and Burke, et al., Ann Surg 194, 413 (1981) relate to methods to generate new tissues in vivo by implanting non-living materials such as modified collagens which are seeded with cells to promote guided regeneration of tissue such as skin. Langer, et al. Science 260, 920 (1993) and Vacanti, et al., Materials Research Society 252, 367 (1992) involve synthetic fibrous matrices to which tissue specific cells were added in vitro. The matrices are highly porous and allow mass transfer to the cells in vitro and after implantation in vivo. After implantation, new blood vessels grow into the devices to generate a new vascularized tissue. However, the relatively long time course for angiogenesis limits the size of the newly formed tissue.

The field of Tissue Engineering is undergoing explosive growth. See, for example, Vacanti, et al., Lancet 354, 32 (1999); Langer, et al, Science 260, 920 (1993); Rennie, J. Scientific American 280, 37 (1999); and Lysaght, et al., Tissue Eng 4, 231 (1998). Virtually every tissue and organ of the body has been studied; many tissue-engineering technologies are becoming available. See Lysaght, et al. Tissue Eng 4, 231 (1998); Bell, et al., Science 221, 1052 (1981); Burke, et al., Ann Surg 194, 413 (1981); Compton, et al., Laboratory Investigation 60, 600 (1989); Parenteau, et al., Journal of Cellular Biochemistry 45, 24 (1991); Parenteau, et al., Biotechnology and Bioengineering 52, 3 (1996); Purdue, et al., J. Burn Care Rehab 18, 52 (1997); Hansbrough and Franco, Clinical Plastic Surg 25, 407 (1998); Vacanti, et al., Materials Research Society 252, 367 (1992).

Over time, several techniques to engineer new living tissue have been studied. Technologies include the use of growth factors to stimulate wound repair and regeneration, techniques of guided tissue regeneration using non-living matrices to guide new tissue development, cell transplantation, and cell transplantation on matrices. More recently, new understanding in stem cell biology has led to studies of populations of primordial cells, stem cells, or embryonic stem cells to use in tissue engineering approaches.

In parallel to these advances, the rapidly emerging field of MicroElectroMechanical Systems (MEMS) has penetrated a wide array of applications, in areas as diverse as automotives, inertial guidance and navigation, microoptics, chemical and biological sensing, and, most recently, biomedical engineering, McWhorter, et al. "Micromachining and Trends for the Twenty-First Century", in Handbook of Microlithography, Micromachining and Microfabrication, ed. P. Rai-Choudhury, (Bellingham, Wash.: SPIE Press, 1997). Microfabrication technology has been used in important studies in cell and developmental biology to understand complex biologic signaling events occurring at the cell membrane-surface interface, as described, for example, by Kane, et al., Biomaterials 20, 2363 (1999). It has also been used in tissue engineering to guide cell behavior and the formation of small units of tissue, as described by Griffith, et al., Annals of Blamed. Eng., 26 (1998).

Microfabrication methods for MEMS represent an extension of semiconductor wafer process technology originally developed for the integrated circuit (IC) industry. Control of features down to the submicron level is routinely achieved in IC processing of electrical circuit elements; MEMS technology translates this level of control into mechanical structures at length scales stretching from less than 1 micron ($\mu$m) to greater than 1 centimeter (cm). Standard bulk micromachining enables patterns of arbitrary geometry to be imprinted into wafers using a series of subtractive etching methods. Three-dimensional structures can be realized by superposition of these process steps using precise alignment techniques. Several groups (Griffith, et al., Annals of Biomed. Eng., 26 (1998); Folch, et al., Biotechnology Progress, 14, 388 (1998)) have used these highly precise silicon arrays to control cell behavior and study gene expression and cell surface interactions. However, this approach is essentially a two-dimensional technology and it is unknown whether it can be adapted to the generation of thick, three-dimensional tissues.

PCT US96/09344 by Massachusetts Institute of Technology involves a three-dimensional printing process, a form of solid free form fabrication, which builds three-dimensional objects as a series of layers. This process uses polymer powders in layers bound by polymer binders whose geometry is dictated by computer-assisted design and manufacture. This technique allows defined internal architectures, which could include branching arrays of channels mimicking a vascular supply. However, this technique is limited by the characteristics and chemistry of the particular polymers. Also, it severely limits the types of tissue to be fabricated. For example, these polymer walls do not allow the plasma exchange that is needed in the alveolar capillary wall of the lung.

A further limitation of the prior art methods of tissue engineering is related to mass transport. Cells must be within approximately 100 $\mu$m of a capillary blood supply. Tissue engineered constructs without a blood supply develop hypoxia and nutrient deprivation. Without vasculature, cells in constructs larger than 1-2 mm experience significant necrosis. To date, all approaches in tissue engineering have relied on the in-growth of blood vessels into tissue-engineered devices to achieve permanent vascularization. This strategy has worked well for many tissues; however, it falls short for thick, complex tissues such as large vital organs, including liver, kidney, and heart. See Eiselt, et al., Biotechnol. Prog. 14, 134 (1998). Novel methods and devices that enable the production of thick, complex tissue-engineered structures would be highly desirable.

OBJECTS AND SUMMARY OF THE INVENTION

To overcome obstacles known in the art, an approach to provide thick structures with preexisting vasculature before implantation was developed using microfabrication techniques, such as three-dimensional printing to provide an ordered array of branching channels in a substrate formed of a suitable material, such as silicon or a biocompatible polymer, which are then seeded with cells. A complete branching vascular circulation is made in two dimensions on the surface of the material using microfabrication. The two-dimensional structure can then be lifted or otherwise separated from the silicon mold and folded or rolled into a compact three-dimensional structure.

The laminated tissue structures comprise multiple layers wherein each layer comprises tissue and vasculature assembled adjacent to each other by folding and compacting. The vasculature is in three dimensions throughout the structure and the structure optionally has connections for flow into and out of the vasculature. The laminated tissue structures can be implanted directly by connecting blood vessels to flow into and out of the vasculature. As such, the present invention overcomes problems known in the art of tissue engineering, which is limited to the production of very thin structures.

An object of the present invention can be to provide a method and materials for making complex, living, vascularized tissues for organ and tissue replacement, especially complex and/or thick structures, such as liver tissue.

The invention provides an apparatus for making tissue lamina comprising a first mold or polymer scaffold, a semi-permeable membrane, and a second mold or polymer scaffold, wherein the semi-permeable membrane is disposed between the first and second molds and/or polymer scaffolds, wherein the first and second molds and/or polymer scaffolds have microchannels or compartments positioned toward the semi-permeable membrane, wherein the first and second molds and/or polymer scaffolds are fastened together, and wherein each of the first and second molds and/or polymer scaffolds and the semi-permeable membrane are comprised of material that is suitable for attachment and culturing of animal cells. The semi-permeable membrane enables transport of small molecules, such as oxygen, through thin bulk layers, but does not require actual pores for transport.

The apparatuses of the invention are made from layers comprising at least a first mold or polymer scaffold, a second mold or polymer scaffold and a semi-permeable membrane. These layers can be assembled such that they are in complete registration (i.e. perfectly aligned), or in partial registration (i.e. imperfectly aligned).

The apparatus can optionally be in fluid communication with nutrient supply and excretion removal lines for culturing animal cells, and can further comprise a pumping means for circulating fluid throughout the apparatus. The direction of flow can be controlled or directed as needed, and can be in all directions. The pumping means can comprise a syringe, a peristaltic pump or any other pumping means known in the art of cell or tissue culture.

The semi-permeable membrane allows gas exchange, diffusion of nutrients, and waste removal. The first mold or polymer scaffold can comprise the circulation through which blood, plasma or media with appropriate levels of oxygen can be continuously circulated to nourish the cells/tissue in one or more additional molds and/or polymer scaffolds. The second mold or polymer scaffold can comprise a reservoir for the functional cells of an organ, and optionally includes inlets for neural inervation or other activity.

The invention further comprises a system for making tissue lamina comprising (a) an apparatus for making tissue lamina comprising a first mold or polymer scaffold, a semi-permeable membrane, and a second mold or polymer scaffold, wherein the semi-permeable membrane is disposed between the first and second molds and/or polymer scaffolds, wherein the first and second molds and/or polymer scaffolds have means defining microchannels positioned toward the semi-permeable membrane, wherein the first and second molds and/or polymer scaffolds are fastened together, and wherein each of the first and second molds and/or polymer scaffolds and the semi-permeable membrane are comprised of material that is suitable for attachment and culturing of animal cells; and (b) animal cells.

The invention also provides a method of making an apparatus for making tissue lamina comprising the steps of (a) positioning a semi-permeable membrane between a first and second mold and/or polymer scaffold, wherein the first and second molds and/or polymer scaffolds have means defining microchannels positioned toward the semi-permeable membrane and wherein each of the first and second molds and/or polymer scaffolds and the semi-permeable membrane are comprised of material that is suitable for attachment and culturing of animal cells; and (b) fastening the first and second molds and/or polymer scaffolds together such that the semi-permeable membrane is disposed between the molds and/or polymer scaffolds.

As described herein, complex tissues are formed by laminating layers of thin vascularized tissues to form thick tissue structures or more complex organ equivalents. The thin vascularized layers of tissue lamina are formed by:

(a) positioning a semi-permeable membrane between a first and second mold and/or polymer scaffold, wherein the first and second molds and/or polymer scaffolds have means defining microchannels positioned toward the semi-permeable membrane, and wherein each of the first and second molds and/or polymer scaffolds and the semi-permeable membrane are comprised of material that is suitable for attachment and culturing of animal cells;

(b) fastening the first and second molds and/or polymer scaffolds together such that the semi-permeable membrane is disposed between the molds and/or polymer scaffolds, thereby forming an apparatus; and (c) culturing cells in the microchannels of the molds and/or polymer scaffolds. Culturing cells in microchannels can comprise (i) seeding animal cells into the microchannels of the first mold or polymer scaffold;

(ii) culturing the animal cells of (i) under conditions such that they form blood vessels or other lumenal structures;

(iii) seeding animal cells into the microchannels of the second mold or polymer scaffold; and (iv) culturing the animal cells of (ii) under conditions such that they form parenchymal tissue.

The apparatus and tissues therein can optionally be connected in fluid communication with nutrient supply and excretion removal lines for culturing animal cells, and fluid can further be circulated through the apparatus by means of a pump. The pump can comprise a syringe, a peristaltic pump or any other pumping means known in the art of cell or tissue culture.

Three dimensional tissue can be formed by gently lifting tissue from the mold and/or polymer scaffold using techniques such as fluid flow and other supporting material, as necessary. Where the polymer scaffold is comprised of biodegradable monomers, hydrolysis of the monomers results in degradation of the scaffold over time.

The tissue can be systematically folded or rolled and compacted into a three-dimensional vascularized structure. This structure can be implanted into animals or patients by directly connecting the blood vessels. Optionally, the semi-permeable membrane can be removed. Immediate perfusion of oxygenated blood occurs, which allows survival and function of the entire living mass.

The two-dimensional surface of the mold can also be varied to aid in the folding and compacting process. For example, the surface can be changed from planar to folded in an accordion-like fashion. It can be stacked into multiple converging plates. It can be curvilinear or have multiple projections.

Alternatively, multiple molds and/or polymer scaffolds can be stacked adjacent to one another, making multiple vascularized layers of tissue lamina until the desired complex structure (e.g. organ equivalent) is formed. These structures can then be implanted and optionally, the vasculature anastomized into the existing vasculature to provide an immediate blood supply for the implanted organ equivalent. Alternatively, these structures comprise extracorporeal support devices.

A preferred method of making multiple layers of tissue lamina in three dimensions is to form an apparatus by positioning a semi-permeable membrane between two molds and/or polymer scaffolds, which molds have microchannels positioned toward the semi-permeable membrane, and wherein the molds and/or polymer scaffolds and the semi-permeable membrane comprise material that is suitable for attachment and culturing of animal cells. The molds and/or polymer scaffolds are fastened together such that the semi-permeable membrane is between them, Cells are then cultured in the microchannels of the molds and/or polymer scaffolds to form tissue lamina, which is removed from the apparatus and folded or rolled to form multiple layers of tissue lamina in three dimensions.

In another embodiment, multiple layers of tissue lamina in three dimensions are created by forming an apparatus from two molds and/or polymer scaffolds and a semi-permeable membrane, as described above, and fastening a third mold or polymer scaffold adjacent to the first or second mold or polymer scaffold. The third mold or polymer scaffold also has microchannels, which are positioned toward the adjacent mold or polymer scaffold. A second semi-permeable membrane can separate the third mold or polymer scaffold from the adjacent mold or polymer scaffold. Microchannels in successive layers can be connected by through holes to create a parallel channel network in three dimensions. Cells are cultured in the microchannels of the first, second and third molds and/or polymer scaffolds to form three dimensional tissue. Additional mold and/or polymer scaffold layers and optionally, semi-permeable membranes, can be added to create thicker tissue.

The systems and methods of the invention can be implanted into a subject to supplement or replace the biological function of a tissue or organ. Alternatively, the systems and methods can remain ex vivo, serving as extracorporeal devices to supplement or replace biological function.

Examples of tissues and organs which can be fabricated using these methods include, but are not restricted to, organs currently transplanted such as heart, liver, pancreas, lung, kidney and intestine. Other tissues such as muscle, bone, breast, reproductive and neural tissue could also be engineered.

These and other embodiments are disclosed or are obvious from and encompassed by, the following Detailed Description.

BRIEF DESCRIPTION OF THE DRAWINGS

The following Detailed Description, given by way of example, but not intended to limit the invention to specific embodiments described, may be understood in conjunction with the accompanying Figures, incorporated herein by reference, in which:

FIG. 3 shows a schematic of a process for fabricating U-shaped trenches to make a branching pattern on silicon wafers.

FIG. 5 shows a schematic of a pattern etched using an inductively-coupled plasma (ICP) system.

FIG. 6 shows a schematic of an etched surface showing a branching structure that branches out from a single inlet and then converges back into a single outlet.

FIGS. 7A, B, and C show schematics of a cross-sectional view of different etched channels in the surface of FIG. 6.

FIGS. 8A, B and C show schematics of a process for making a tissue layer.

FIG. 9B shows the apparatus of 9A seeded with vascular cells or cells that form lumen (e.g. biliary ducts) (4) and functional cells (e.g. hepatocytes) (5).

FIGS. 10A and 10B show the membrane surface at 650× and 6500× magnification, respectively. FIG. 10C shows the membrane in cross-section at 650× magnification.

FIGS. 12A-G show schematics of various surfaces and how tissue layers might be assembled from them.

FIG. 17A shows cells in culture at Day 3. FIG. 17B shows cells in culture at Day 5. FIG. 17C shows cells in culture at Day 10. Scale bar, 100 μm (original magnification ×100).

FIG. 18A shows macroscopic appearance and FIG. 18B shows microscopic appearance (original magnification ×30).

FIG. 20A shows constructs at 2 weeks. Arrows indicate bile ductular structures. FIG. 20B shows constructs at 1 month. Arrows indicate bile ductular structures. FIG. 20C shows constructs at 2 months. The large clusters of hepatocytes over five cell layers thick were observed at 1 and 2 months. FIG. 20D shows constructs at 1 month. The implanted construct was occupied by the bile ductular structures.

FIG. 21A shows pan-cytokeratin staining at 1 month. FIG. 21B shows albumin staining at 1 month. Arrows indicate bile ductular structures. FIG. 21C shows transferrin staining at 1 month. Arrows indicate bile ductular structures. FIG. 21D shows GGT staining at 1 month. Arrows indicate bile ductular structures with luminal staining. Arrow heads indicate slightly stained hepatocytes.

FIG. 23A is at magnification (×2500). FIG. 23B is at high magnification (×15000).

DETAILED DESCRIPTION

Figure 1A:
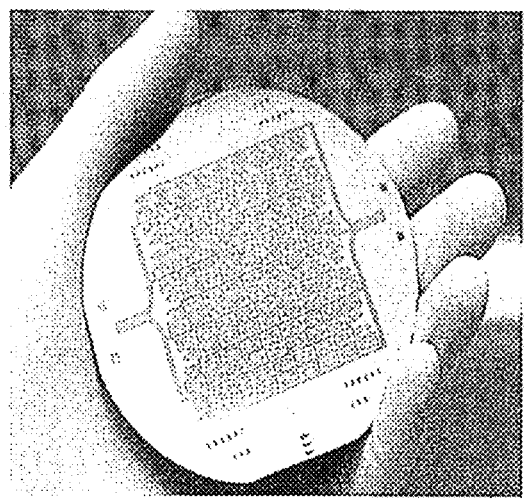
FIG. 1A shows a silicon wafer with a network of microchannels.

The invention provides for the construction of structures comprising tissue in thick layers; enabling fabrication of an entire organ, or portion thereof, having sufficient oxygen transport, nutrient and metabolite movement. The methods of the invention employ a new approach for fabricating three-dimensional vascularized tissues for transplantation in human recipients in need of vital organs and other tissues requiring a blood supply. A two-dimensional (x, y) mold is fabricated using high-resolution molding processes, such as micromachined wafer technology, thick photoresist processes, or other techniques, to create a patterned of micromachined, small dimensioned channels ("microchannels"), such that the micromachined channels are connected for the circulation of fluid in the multilayer apparatus. Microchannels can comprise, for example, open-faced channels defined by walls extending from a tissue-defining surface into a substrate. The invention also encompasses a substrate wherein the tissue-defining surface comprises an open-faced compartment defined by walls extending from a tissue-defining surface into a substrate.

Thus, the invention provides low-cost, scalable techniques for producing organs, or portions thereof, large enough to transplant into a subject, such as animal recipients, typically vertebrate recipients, and preferably human recipients. A "subject" is a vertebrate, preferably a mammal, and most preferably a human. Mammals include, but are not limited to, humans, farm animals, sport animals, and pets. One of skill in the art can readily vary the parameters of the methods described herein to accommodate hosts or subjects of variable size and species, including but not limited to, humans of any age.

Advantages of this invention over other methods of tissue engineering include (a) the capability for producing all of the high resolution three-dimensional structures required for complex tissues and vital organs, and (b) the ability of the mechanical (optionally biodegradable) mold or polymer scaffold to provide support for cell growth and tissue formation, rather than reliance upon biochemical factors alone.

As used herein, the terms "comprises", "comprising", and the like can have the meaning ascribed to them in U.S. Patent Law and can mean "includes", "including" and the like.

Manufacture of Molds and Polymer Scaffolds

For purposes of this invention a "mold" is a device on the surface of which the branching structure of the microchannels is etched or formed. Fabrication of a mold begins by selection of an appropriate substrate. The choice of a substrate material is guided by many considerations, including the requirements placed on the fabrication process by the desired mold dimensions, the desired size of the ultimate template, and the surface properties of the wafer and their interaction with the various cell types, extracellular matrix ("ECM") and polymeric backbone. Also important are the thermal properties, such as the glass transition temperature (Tg), which must be high enough so that the network of pores in the mold does not collapse upon solvent removal.

Molds of the present invention can comprise a variety of materials, including, but not limited to, inert materials such as silicon, polymers such as polyethylene vinyl acetate, polycarbonate, and polypropylene, and materials such as a ceramic or material such as hydroxyapatite. In particular, the mold can comprise from metals, ceramics, semiconductors, organics, polymers, and composites. Representative metals and semiconductors include pharmaceutical grade stainless steel, gold, titanium, nickel, iron, gold, tin, chromium, copper, alloys of these or other metals, silicon, silicon dioxide. These materials are either inherently suitable for the attachment and culture of animal cells or can be made suitable by coating with materials described herein to enhance cell attachment and culture (e.g. gelatin, matrigel, vitrogen and other tissue culture coatings known in the art).

Figure 1B:
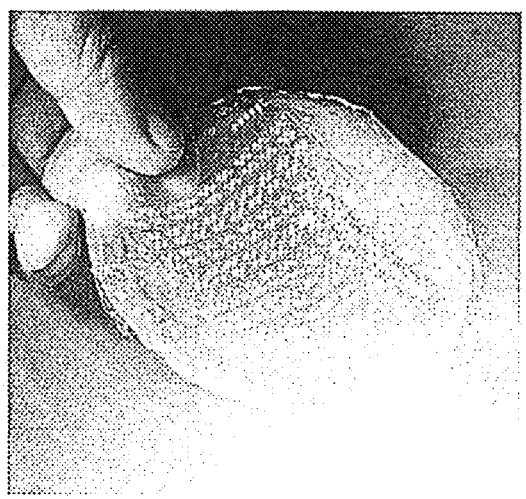
FIG. 1B shows a polymer scaffold with a network of microchannels.
Figure 2:
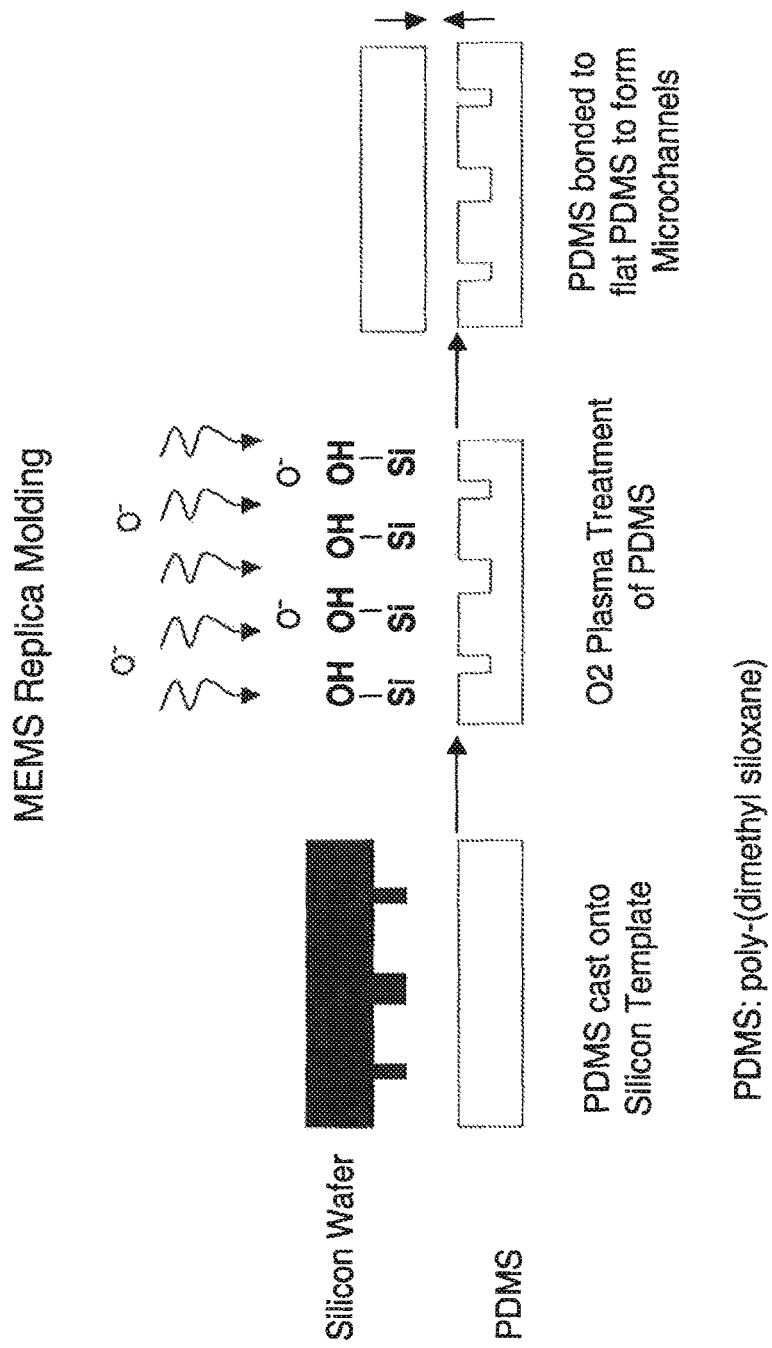
FIG. 2 shows a schematic diagram of one method for making a polymer scaffold from a micromachined silicon wafer using MEMS replica molding.

In an alternative embodiment, MEMS replica molding can be used to make a "polymer scaffold" for seeding cells. In this method, a mold is made as described herein, preferably of silicon (FIG. 1A), and is then used as a template on which a polymeric material is cast (FIG. 2). Optionally, the polymer scaffold can then be peeled away from the mold (FIG. 1B) and seeded with cells.

A "tissue-defining surface" is the surface of a mold or a polymer scaffold, and a "substrate" is the mold or polymer scaffold itself.

The term "polymer" includes polymers and monomers that can be polymerized or adhered to form an integral unit. The polymer can be non-biodegradable or biodegradable, typically via hydrolysis or enzymatic cleavage. Biodegradable matrices are not typically preferred to construct molds, since they are not implanted and are preferably reusable. For implantation, polymer scaffolds are preferably used, more preferably biodegradable polymer scaffolds.

In a preferred embodiment, the biodegradable polymer scaffold comprises biodegradable elastomers formed from hydrolyzable monomers as described in Wang et al., Nature Biotech 20, 602 (2002), the contents of which are incorporated herein by reference. These biodegradable elastomers are analogous to vulcanized rubber in that crosslinks in a three dimensional network of random coils are formed. These biodegradable elsatomers are hydrolyzed over time, preferably within 60 days.

Polymer material for implantation should be selected for biocompatibility. Any degradation products should also be biocompatible. Relatively high rigidity is advantageous so that the polymer scaffold can withstand the contractile forces exerted by cells growing within the mold. A biocompatible degradable polymer and its degradation products are non-toxic toward the recipient.

The term "biodegradable" refers to materials that are bioresorbable and/or degrade and/or break down by mechanical degradation upon interaction with a physiological environment into components that are metabolizable or excretable, over a period of time from minutes to three years, preferably less than one year, while maintaining the requisite structural integrity. As used in reference to polymers, the term "degrade" refers to cleavage of the polymer chain, such that the molecular weight stays approximately constant at the oligomer level and particles of polymer remain following degradation. The term "completely degrade" refers to cleavage of the polymer at the molecular level such that there is essentially complete loss of mass. The term "degrade" as used herein includes "completely degrade" unless otherwise indicated.

Materials suitable for polymer scaffold fabrication include, but are not limited to, poly-dimethyl-siloxane (PDMS), poly-glycerol-sebacate (PGS), polylactic acid (PLA), poly-L-lactic acid (PLLA), poly-D-lactic acid (PDLA), polyglycolide, polyglycolic acid (PGA), polylactide-co-glycolide (PLGA), polydioxanone, polygluconate, polylactic acid-polyethylene oxide copolymers, modified cellulose, collagen, polyhydroxybutyrate, polyhydroxprio-pionic acid, polyphosphoester, poly(αhydroxy acid), poly-caprolactone, polycarbonates, polyatnides, polyanhydrides, polyamino acids, polyorthoesters, polyacetals, polycyano-acrylates, degradable urethanes, aliphatic polyesterspoly-acrylates, polymethacrylate, acyl substituted cellulose acetates, non-degradable polyurethanes, polystyrenes, polyvinyl chloride, polyvinyl fluoride, polyvinyl imidazole, chlorosulphonated polyolifins, polyethylene oxide, polyvinyl alcohol, teflon RTM, nylon silicon, and shape memory materials, such as poly(styrene-block-butadiene), polynor-bornene, hydrogels, metallic alloys, and oligo(ε-caprolactone)diol as switching segment/oligo(p-dioxyanone)diol as physical crosslink. Other suitable polymers can be obtained by reference to The Polymer Handbook, 3rd edition (Wiley, N.Y., 1989). Combinations of these polymers may also be used.

Polylactide-co-glycolides (PLGA), as well as polylactides (PLA) and polyglycolides (PGA) have been used to make biodegradable implants for drug delivery. See U.S. Pat. No. 6,183,781 and references cited therein. Biodegradable materials have been developed for use as implantable prostheses, as pastes, and as templates around which the body can regenerate various types of tissue. Polymers that are both biocompatible and resorbable in vivo are known in the art as alternatives to autogenic or allogenic substitutes. In a preferred embodiment, polymers are selected based on the ability of the polymer to elicit the appropriate biological response from cells, for example, attachment, migration, proliferation and gene expression.

Solvents for most of the thermoplastic polymers are known, for example, methylene chloride or other organic solvents Organic and aqueous solvents for protein and polysaccharide polymers are also known. The binder can be the same material as is used in conventional powder processing methods or can be designed to ultimately yield the same binder through chemical or physical changes that occur as a result of heating, photopolymerization, or catalysis.

Properties of the mold and/or polymer scaffold surface can be manipulated through the inclusion of materials on the mold or in polymer scaffold material which alter cell attachment (for example, by altering the surface charge or structure), porosity, flexibility or rigidity (which may be desirable to facilitate removal of tissue constructs). Moreover, advances in polymer chemistry can aid in the mechanical tasks of lifting and folding as well as the biologic tasks of adhesion and gene expression.

For example, molds can be coated with a unique temperature-responsive polymer, poly-N-isopropyl acrylamide (PNIPAAm), which demonstrates a fully expanded chain conformation below 32° C. and a collapsed, compact confirmation at high temperatures. When grafted onto surfaces of silicon wafers using electron beam irradiation, it can be used as a temperature switch for creating hydrophilic surfaces below 32° C. and hydrophobic surfaces above 32° C. Since PNIPAAm is insoluble in water over the lower critical solution temperature (LCST about 32° C.) and reversibly solubilized below the LCST, cells detach from the substratum by simply lowering the temperature below the LCST. One of skill in the art can (1) engraft the polymer on silicon wafers that are pre-coated with polystyrene or (2) engraft the polymer on silicon wafers whose surface is first modified by vinyl-tricholorosilane. Either of these techniques will ensure that the polymer is better integrated and conjugated to its substratum (polystyrene in the former case and vinyl groups in the later case) so that it can serve as an effective thermal switch, useful in reversing cell attachment and detachment as a single contiguous layer of cells without the usual cell damage.

Another system for promoting both cellular adhesion and lifting of cells as intact sheets can involve the use of RGD (Arg-Gly-Asp) peptides. The RGD sequence is part of the domain within the fibronectin molecule that endows it with the ability to interact with adhesion molecules present on the cell surface of fibroblasts. Fibronectin itself is a well-characterized extracellular, structural glycoprotein which interacts strongly with other extracellular matrix molecules and which causes the attachment and spreading of most cells. This function of the fibronectin molecule is localized primarily to the RGD sequence. One of skill in the art can synthesize RGD peptides with a structural backbone of PMMA that has an RGD peptide sequence at its tips, bound one another with the intermediate layering of polyethylene oxide. This allows differential cell adhesion in only selected areas and not others. Once the tissue of desired quality is formed, release of this intact monolayer of tissue from its substratum is straightforward; it requires only the addition of soluble RGD to the culture medium to act as a competitive substrate to the insolubilized RGD substrate on the silicon mold surface.

In some embodiments, attachment of the cells to the mold and/or polymer scaffold is enhanced by coating the substrate with compounds such as basement membrane components, agar, agarose, gelatin, gum arabic, types I, II, III, IV, and V collagen, fibronectin, laminin, glycosaminoglycans, matrigel, vitrogen, mixtures thereof, and other materials known to those skilled in the art of cell culture.

Thus, by the methods of the invention, cells can be grown on molds that are uncoated or coated as described herein, depending upon the material used for mold construction. Alternatively, cells can be grown on polymer scaffolds made by replica molding techniques.

Micromachining, and Chemical Processing of Silicon and Other Mold Materials

Molds can be made by creating small mechanical structures in silicon, metal, polymer, and other materials using microfabrication processes. (FIG. 3.) These microfabrication processes are based on well-established methods used to make integrated circuits and other microelectronic devices, augmented by additional methods developed by workers in the field of micromachining.

Microfabrication processes that can be used in making the molds disclosed herein include lithography; etching techniques, such as lasers, plasma etching, photolithography, or chemical etching such as wet chemical, dry, and photoresist removal; or by solid free form techniques, including three-dimensional printing (3DP), stereolithography (SLA), selective laser sintering (SLS), ballistic particle manufacturing (BPM) and fusion deposition modeling (FDM); by micromachining; thermal oxidation of silicon; electroplating and electroless plating; diffusion processes, such as boron, phosphorus, arsenic, and antimony diffusion; ion implantation; film deposition, such as evaporation (filament, electron beam, flash, and shadowing and step coverage), sputtering, chemical vapor deposition (CVD), epitaxy (vapor phase, liquid phase, and molecular beam), electroplating, screen printing, lamination or by combinations thereof. See Jaeger, *Introduction to Microelectronic Fabrication* (Addison-Wesley Publishing Co., Reading Mass. 1988); Runyan, et al, *Semiconductor Integrated Circuit Processing Technology* (Addison-Wesley Publishing Co., Reading Mass. 1990); Proceedings of the IEEE Micro Electro Mechanical Systems Conference 1987-1998; Rai-Choudhury, ed., *Handbook of Microlithography, Micromachining & Microfabrication* (SPIE Optical Engineering Press, Bellingham, Wash. 1997). The selection of the material that is used as the mold determines how the surface is configured to form the branching structure. The following methods are preferred for making molds.

Typically, micromachining is performed on standard bulk single crystal silicon wafers of a diameter ranging between about 50 and 300 millimeters (mm), preferably approximately 60 mm, and of thickness ranging between about 300 and 1200 µm. These wafers can be obtained from a large number of vendors of standard semiconductor material, and are sawn and polished to provide precise dimensions, uniform crystallographic orientation, and highly polished, optically flat surfaces. Wafers made from pyrex borosilicate or other glasses can also be procured and inserted into micromachining processes, with alternative processes used to etch the glassy materials.

The geometry of the mold, in particular the number of different feature depths required, is the major factor determining the specific process sequence. The simplest case is that of a single depth dimension for the mold. Specifically, for a silicon substrate, the process sequence (shown in FIG. 3) is as follows: first, the silicon wafer is cleaned, and a layer of photosensitive material is applied to the surface. Typically, the layer is spun on at a high revolution rate to obtain a coating of uniform thickness. The photoresist is baked, and the wafer is then exposed to ultraviolet or other short-wavelength light though a semi-transparent mask. This step can be accomplished using any one of several masking techniques, depending on the desired image resolution. The resist is then developed in an appropriate developer chemistry, and the wafer is then hard-baked to remove excess solvent from the resist. Once the lithographic process has been completed, the wafer can be etched in a plasma reactor using one of several possible chemistries. Etching serves to transfer the two-dimensional pattern into the third dimension: a specified depth into the wafer. Plasma parameters are determined by the desired shape of the resulting trench (semi-circular, straight-walled profile, angled sidewall), as well as by the selectivity of the etchant for silicon over the masking photoresist. Once the etching has been completed, the photoresist can be removed and the wafer prepared for use in the tissue molding, process.

Figure 4:
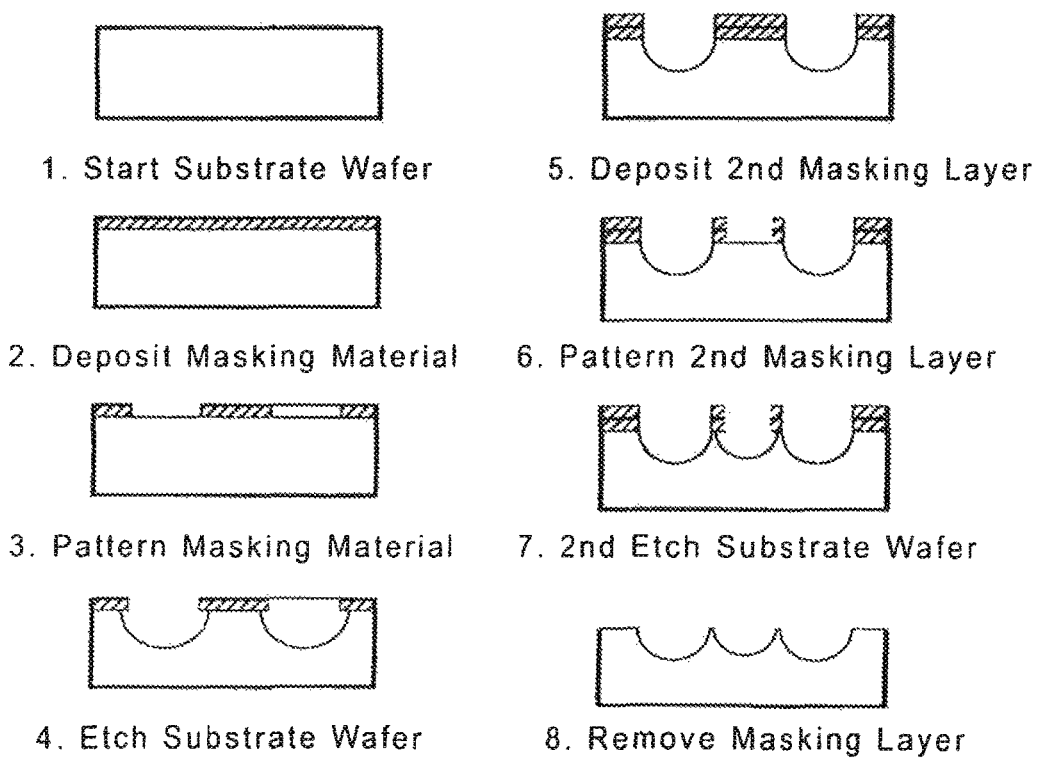
FIG. 4 shows a more detailed schematic describing a process for the production of a complex structure comprising channels of varying depths.

Increased flexibility in the geometry of wafer mold can be obtained by inserting additional cycles of masking and etching, as shown in FIG. 4. Here, a second step in which a masking layer has been applied, and open areas etched, is shown. This modification provides the opportunity to machine channels of varying depths into the wafer mold. To design a mold that is suitable for the culturing of endothelial cells, increased flexibility is very important due to the need for vascular branches with different diameters. The techniques can be extended to provide as many additional layers and different depths as are desired. In addition, these techniques can be used to create secondary patterns within the pattern of microchannels. For example, it may be advantageous to have wells within the microchannels for culturing additional cell types such as feeder cells. The pattern of microchannels also can be designed to control cell growth, for example, to selectively control the differentiation of cells.

Glass and polymeric wafer molds can be fabricated using a similar sequence, but the actual process can be modified by the addition of an intervening masking layer, since etchants for these materials may attack photoresist as well. Such intervening materials simply function to transfer the pattern from the photoresist to interlayer and then on to the wafer below. For silicon etched in one of several wet chemistries, an intervening layer may also be necessary.

Electrolytic anodization of silicon in aqueous hydrofluoric acid, potentially in combination with light, can be used to etch channels into the silicon. By varying the doping concentration of the silicon wafer to be etched, the electrolytic potential during etching, the incident light intensity, and the electrolyte concentration, control over the ultimate pore structure can be achieved. This process uses deep plasma etching of silicon. Needles are patterned directly using photolithography, rather than indirectly by controlling the voltage (as in electrochemical etching), thus providing greater control over the final mold geometry.

In this process, an appropriate masking material (e.g., metal) is deposited onto a silicon wafer substrate and patterned into dots having the diameter of the desired channels. The wafer is then subjected to a carefully controlled plasma based on fluorine/oxygen chemistries to etch very deep, high aspect ratio trenches into the silicon. See, e.g., Jansen, et al., "The Black Silicon Method IV: The Fabrication of Three-Dimensional Structures in Silicon with High Aspect Ratios for Scanning Probe Microscopy and Other Applications," IEEE Proceedings of Micro Electro Mechanical Systems Conference, pp. 88-93 (1995).

A metal layer is first evaporated onto a planar substrate. A layer of photoresist is then deposited onto the metal to form a patterned mold, which leaves an exposed-metal region in the shape of needles. By electroplating onto the exposed regions of the metal seed layer, the mold bounded by photoresist can be filled with electroplated material. Finally, the substrate and photoresist mold are removed, leaving the finished mold array. The molds produced by this process generally have channels with diameters on the order of about 1 µm or larger. Preferably, microchannels have a diameter of about 1 µm to about 500 µm. See Frazier, et al., "Two dimensional metallic microelectrode arrays for extracellular stimulation and recording of neurons", IEEE Proceedings of the Micro Electro Mechanical Systems Conference, pp. 195-200 (1993).

Another method of forming solid silicon molds is by using epitaxial growth on silicon substrates, as is utilized by Containerless Research, Inc. (Evanston, Ill., USA) for its products.

The size distribution of the etched porous structure is highly dependent on several variables, including doping kind and illumination conditions, as detailed in Lehmann, "Porous Silicon—A New Material for MEMS", IEEE Proceedings of the Micro Electro Mechanical Systems Conference, pp. 1-6 (1096). Porous polymer molds can be formed, for example, by micromolding a polymer containing a volatilizable or leachable material, such as a volatile salt, dispersed in the polymer, and then volatilizing or leaching the dispersed material, leaving a porous polymer matrix in the shape of the mold. Hollow molds can be fabricated, for example, using combinations of dry etching processes (Laermer, et al., "Bosch Deep Silicon Etching: Improving Uniformity and Etch Rate for Advanced MEMS Applications," Micro Electro Mechanical Systems, Orlando, Fla., USA, (Jan. 17-21, 1999); Despont, et al., "High-Aspect-Ratio, Ultrathick, Negative-Tone Near-UV Photoresist for MEMS", Proc. of IEEE 10$^{th}$ Annual International Workshop on MEMS, Nagoya, Japan, pp. 518-522 (Jan. 26-30, 1997)); micromold creation in lithographically-defined polymers and selective sidewall electroplating; or direct micromolding techniques using epoxy mold transfers.

A chromium mask can be substituted for the solid molds using a silicon nitride layer covered with chromium. Solid molds are then etched, the chromium is stripped, and the silicon is oxidized. The silicon nitride layer will prevent oxidation. The silicon nitride is then stripped, leaving exposed silicon and oxide-covered silicon everywhere else. The needle is then exposed to an ICP plasma which selectively etches the silicon in a highly anisotropic manner to form the interior hole of the needle. A second method uses solid silicon as 'faints' around which the actual needle structures are deposited. After deposition, the forms are etched away, yielding the hollow structures. Silica needles or metal needles can be formed using different methods. The wafers are then oxidized to a controlled thickness, the silicon nitride is then stripped and the silicon core selectively etched away (e.g., in a wet alkaline solution) to form a hollow silica mold.

In another embodiment, deep reactive ion etching is combined with a modified black silicon process in a conventional reactive ion etcher. First, designs are patterned through photoresist into $SiO_2$, such as on a silicon wafer. Then the silicon can be etched using deep reactive ion etching (DRIE) in an inductively coupled plasma (ICP) reactor to etch deep vertical holes or channels. The photoresist is then removed. Next, a second photolithography step patterns the remaining $SiO_2$ layer. The photoresist is then removed and the silicon wafer again deep silicon etched completely through the wafer in the regions not covered with $SiO_2$). (See FIG. 5.) This process can be varied as follows. After the wafer is patterned, the photoresist and $SiO_2$ layers are replaced with conformal DC sputtered chromium. The second JCP etch is replaced with a $SF_6/O_2$ plasma etch in a reactive ion etcher (RIE), which results in positively sloping outer sidewalls. Henry, et al., "Micromachined Needles for the Transdermal Delivery of Drugs," Micro Electra Mechanical Systems, Heidelberg, Germany, pp. 494-498 (Jan. 26-29, 1998). Alternatively, silicon may be etched anisotropically using Deep Reactive Ion Etching (DRIE) using a switched-process technology (A. A. Ayon, S. Nagle, L. Frechette, A. Epstein and M. A. Schmidt, "Tailoring etch directionality in a deep reactive ion etching tool," J. Vac. Sci. Tech. B 18, 1412 (2000)).

Metal shapes can be formed by physical vapor deposition of appropriate metal layers on solid forms, which can be made of silicon using the techniques described above, or which can be formed using other standard mold techniques such as embossing or injection molding. The metals are selectively removed using electropolishing techniques, in which an applied anodic potential in an electrolytic solution will cause dissolution of metals due to concentration of electric field lines. Once the underlying silicon forms have been exposed, the silicon is selectively etched away to form structures. This process could also be used to make structures made from other materials by depositing a material other than metal on the needle forms and following the procedure described above.

Molds formed of silicon dioxide can be made by oxidizing the surface of the silicon mold forms, rather than depositing a metal and then etching away the solid needle forms to leave the hollow silicon dioxide structures. In one embodiment, hollow, porous, or solid molds are provided with longitudinal grooves or other modifications to the exterior surface of the molds.

Polymeric molds can also be made using microfabrication. For example, the epoxy molds can be made as described above, and injection molding techniques can be applied to form the structures. These micromicromolding techniques are relatively less expensive to replicate than the other methods described herein.

Three dimensional printing (3DP) is described by Sachs, et al., Manufacturing Review 5, 117-126 (1992) and U.S. Pat. No. 5,204,055 to Sachs, et al. 3DP is used to create a solid object by ink jet printing a binder into selected areas of sequentially deposited layers of powder. Each layer is created by spreading a thin layer of powder over the surface of a powder bed. The powder bed is supported by a piston, which descends upon powder spreading and printing of each layer (or, conversely, the ink jets and spreader are raised after printing of each layer and the bed remains stationary). Instructions for each layer are derived directly from a computer-aided design (CAD) representation of the component. The area to be printed is obtained by computing the area of intersection between the desired plane and the CAD representation of the object. The individual sliced segments or layers are joined to form the three-dimensional structure. The unbound powder supports temporarily unconnected portions of the component as the structure is built but is removed after completion of printing.

SPF methods other than 3DP that can be utilized to some degree as described herein are stereo-lithography (SLA), selective laser sintering (SLS), ballistic particle manufacturing (BPM), and fusion deposition modeling (FDM). SLA is based on the use of a focused ultraviolet (UV) laser that is vector scanned over the top of a bath of a photopolymerizable liquid polymer material. The UV laser causes the bath to polymerize where the laser beam strikes the surface of the bath, resulting in the creation of a first solid plastic layer at and just below the surface. The solid layer is then lowered into the bath and the laser generated polymerization process is repeated for the generation of the next layer, and so on, until a plurality of superimposed layers forming the desired apparatus is obtained. The most recently created layer in each case is always lowered to a position for the creation of the next layer slightly below the surface of the liquid bath. A system for stereolithography is made and sold by 3D Systems, Inc., of Valencia, Calif., which is readily adaptable for use with biocompatible polymeric materials. SLS also uses a focused laser beam, but to sinter areas of a loosely compacted plastic powder, the powder being applied layer by layer. In this method, a thin layer of powder is spread evenly onto a flat surface with a roller mechanism. The powder is then raster-scanned with a high-power laser beam. The powder material that is struck by the laser beam is fused, while the other areas of powder remain dissociated. Successive layers of powder are deposited and raster-scanned, one on top of another, until an entire part is complete. Each layer is sintered deeply enough to bond it to the preceding layer. A suitable system adaptable for use in making medical devices is available from DTM Corporation of Austin, Tex.

BPM uses an ink-jet printing apparatus wherein an ink-jet stream of liquid polymer or polymer composite material is used to create three-dimensional objects under computer control, similar to the way an ink: jet printer produces two-dimensional graphic printing. The mold is formed by printing successive cross-sections, one layer after another, to a target using a cold welding or rapid solidification technique, which causes bonding between the particles and the successive layers. This approach as applied to metal or metal composites has been proposed by Automated Dynamic Corporation of Troy, N.Y. FDM employs an x-y plotter with a z motion to position an extrudable filament formed of a polymeric material, rendered fluid by heat or the presence of a solvent. A suitable system is available from Stratasys, Incorporated of Minneapolis, Minn.

The design of the channels in the mold can be constructed by a number of means, such as fractal mathematics, which can be converted by computers into two-dimensional arrays of branches and then etched onto wafers. Also, computers can model from live or preserved organ or tissue specimens three-dimensional vascular channels, convert to two-dimensional patterns and then help in the reconversion to a three-dimensional living vascularized structure. Techniques for producing the molds include techniques for fabrication of computer chips and microfabrication technologies. Other technologies include laser techniques.

Design of Apparatus

As shown in FIG. 6, in a preferred embodiment, the pattern in the mold (10), formed of a silicon wafer (11), begins with one or more large channels (12), which serially branch into a large array of channels as small as individual capillaries (14a, 14b, 14c, etc.), then converge to one or more large channels (16). The cross-section of the single "arterial" channel (12) and "venous" channel (16) is shown in FIG. 7A. The cross-section of the portion of mold (10) containing the "capillary" channels (14a, 14b, 14c, etc.), is shown in FIG. 7A. The mold is shown in cross-section in FIG. 7C, with a depth of approximately 5 μm.

The etched surface serves as a template for the circulation of an individual tissue or organ. Living endothelial cells seeded into these channels and provided with flow of appropriate nutrients and gases will line the channels to form blood vessels. In one embodiment, as shown in FIG. 8A, mold and/or polymer scaffold pieces (30 and 32) are fitted together to make an enclosure (34), and the cells are cultured. The vascular cells form vascular channels (36) based on the pattern etched in the mold, as shown in FIG. 8B. In Example 1, it has been demonstrated that cells seeded onto surfaces of silicon and pyrex will lay down matrix and form sheets of tissue of the cell type of origin, either hepatic or endothelial. Once formed and sustained by their own matrix, the top of the mold or polymer scaffold (32) can be removed, and the organ or tissue specific cells can then be added to the etched surface, where they attach and proliferate to form a thin, vaseularized sheet of tissue (36). As shown in FIG. 8C, the tissue can then be gently lifted from the mold or polymer scaffold using techniques such as fluid flow and other supporting material, as necessary. Alternatively, the polymer can be degraded. These sheets can then be formed into three-dimensional units of tissue. In effect, the wafer of silicon or pyrex or the polymer scaffold has acted as a template for the formation of tissue.

Figure 9A:
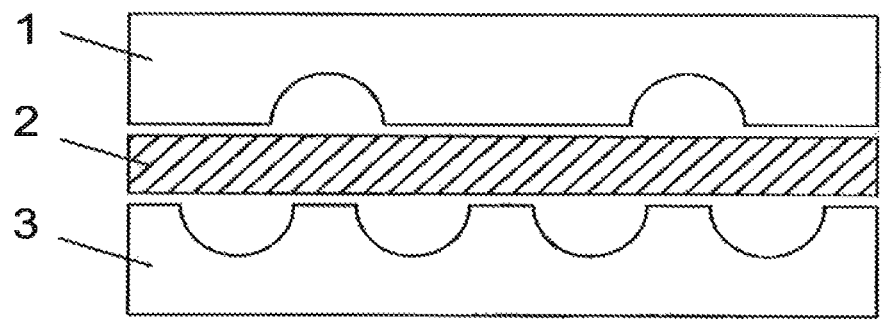
FIGS. 9A and 9B show schematic diagrams of a cross section of an apparatus for tissue engineering and artificial organ support. The apparatus in FIG. 9A comprises a compartment for circulatory flow (1), a semi-permeable membrane for mass transfer of oxygen, nutrients and waste (2), and a compartment for functional cells and excretory system.

In a more preferred embodiment, as shown in FIG. 9A, mold and/or polymer scaffold pieces (1 and 3) are fitted together and separated by a semi-permeable membrane (2). The vascular cells are seeded into one layer and cultured to form vascular channels (4) based on the pattern etched in the surface of the mold, as shown in FIG. 9A. The organ or tissue specific cells are added to the second patterned surface, where they attach and proliferate (5) to form a vaseularized tissue bilayer. The second patterned surface optionally comprises inlets for optionally includes inlets for neural inervation, urine flow, biliary excretion or other activity.

Semi-Permeable Membrane

A semi-permeable membrane can be used to separate the first mold or polymer scaffold from the second mold or polymer scaffold in the microfabricated apparatuses of the invention. Preferably, the pore size of the membrane is smaller than the cell diameters, thus, cells will not be able to pass through (i.e. a low permeability for animal cells), while low molecular weight nutrients and fluids can pass through (i.e. a high permeability for nutrients), thereby providing adequate cell-to-cell signaling. Cell sizes vary but in general, they are in the range of microns. For example, a red blood cell has a diameter of 8 μm. Preferably, the average membrane pore size is on a submicron-scale to ensure effective screening of the cells.

Semi-permeable membranes of the present invention comprise a wide array of different membrane types and morphologies, which can be classified as follows:

(1) Track-etch membranes consisting of cylindrical through-holes in a dense polymer matrix. These membranes are typically made by ion-etching; or (2) Fibrous membranes made by various deposition techniques of polymeric fibers. While these membranes do not have a well-defined pore topology, production methods have been sufficiently refined so that fibrous membranes have specific molecular weight cut-offs.

Track-etch type membranes are preferred, as they limit the fluid motion in one direction. Preferably, fluid motion is in the vertical direction. Fibrous membranes permit fluid motion both laterally and vertically.

The development of an appropriate membrane will mirror the device progression. Biocompatible and non-degradable membranes can be incorporated in microchannels that are made from poly(dimethyl siloxane) (PDMS). Since PDMS is non-degradable, the membranes do not need to be degradable either. However, degradable membranes and materials for microchannels can also be used. There exists a variety of commercial track-etch membranes with well-defined pore sizes that can be used for this purpose. Care must be taken to properly incorporate the membranes into the existing microchannels without leaking. To this end, the membranes can be bonded with either an oxygen plasma or a silicone-based adhesive. A small recession can be designed into the microchannels so that the membrane can fit tightly therein.

In principle, membrane formation from polymers relies on phase-phase separation. Polymer-solvent interactions are complex, and polymer phase diagrams are significantly more complicated than those for monomeric materials, e.g., metals. Phase separation can be induced either by diffusion (diffusion-induced phase separation or "DIPS") or by thermal means (thermal induced phase separation or "TIPS").

Figure 10A:
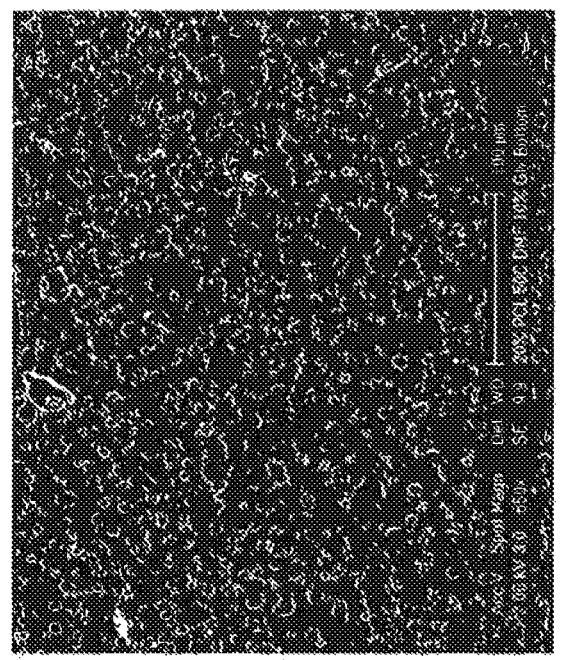
FIGS. 10A-10C show electron micrographs of a semi-permeable membrane made using the TIPS procedure.
Figure 10B:
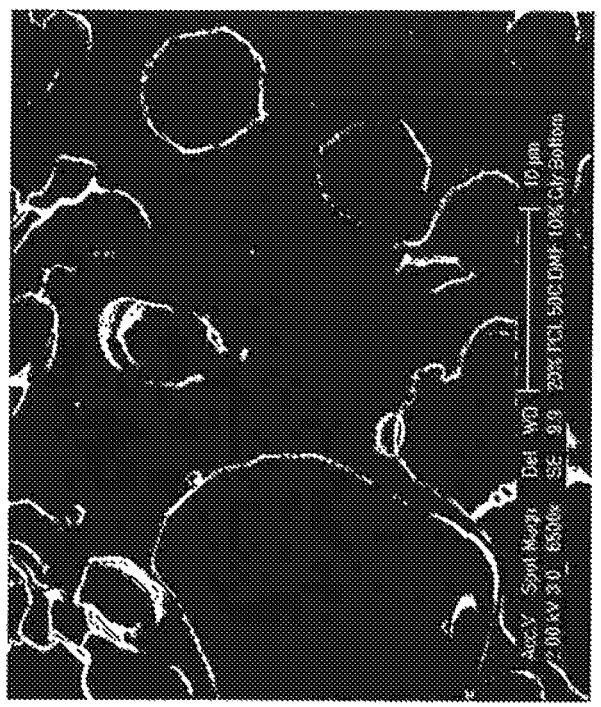
Figure 10C:

A DIPS system comprises polymer, solvent and non-solvent. The polymer solution is cast as a thin film and then immersed in a coagulation bath containing the non-solvent. This process is governed by the diffusion of various low molecular weight components. The exchange of solvent and non-solvent between the polymer solution and the coagulation bath leads to a change in the composition in the film and phase separation is induced. After some time, the composition of the polymer-rich phase reaches the glass transition composition and the system solidifies. To avoid macrovoid formation, a small amount of non-solvent can be mixed with the polymer solution. In a preferred embodiment, the polymer is polycaprolactone (PCL) and the separation system is chloroform/methanol. Specifically, a polymer solution with a concentration ranging from about 5-10% wt. is made. PCL is prepared by dissolving it in chloroform at room temperature under gentle stirring. Once the polymer has completely dissolved, a small amount is placed on a clean mirror surface, and a membrane knife is used to spread out a film with preset thickness. The thickness of the film can be adjusted by changing the gap between the knife blade and the mirror surface. Once the film has been spread, the entire mirror is immersed in a methanol bath. Phase separation occurs almost instantaneously, but the film and mirror are left in the coagulation bath for up to about 10 minutes to lock in the morphology. A typical membrane thickness is about 100 μm, and the pore size is on the order of about 1 μm, preferably between about 0.01 and 20 μm (FIG. 10). Membrane morphology can be varied by altering the composition/concentration of the polymer solution, the film thickness, the components of the coagulation bath, and/or the process conditions. One skilled in the art would understand how to vary any one of the parameters to achieve the desired result.

A TIPS system comprises a thermal gradient to induce phase separation. By choosing a polymer-solvent system that is miscible at high temperatures, but immiscible at low temperatures, e.g., room temperature, phase separation can be induced upon cooling down the polymer solution. In a preferred embodiment, the polymer is PCL and the separation system is DMF/10% $C_3H_8O_3$.

Cells to be Seeded onto the Mold or Polymer Scaffold

The tissue will typically include one or more types of functional, mesenchymal or parenchymal cells, such as smooth or skeletal muscle cells, myocytes (muscle stem cells), fibroblasts, chondrocytes, adipocytes, fibromyoblasts, ectodermal cells, including ductile and skin cells, hepatocytes, kidney cells, pancreatic islet cells, cells present in the intestine, and other parenchymal cells, osteoblasts and other cells forming bone or cartilage, and hematopoietic cells. In some cases it may also be desirable to include nerve cells. The vasculature will typically be formed from endothelial cells. "Parenchymal cells" include the functional elements of an organ, as distinguished from the framework or stroma. "Mesenchymal cells" include connective and supporting tissues, smooth muscle, vascular endothelium and blood cells.

Cells can be obtained by biopsy or harvest from a living donor, cell culture, or autopsy, all techniques well known in the art. Cells are preferably autologous. Cells to be implanted can be dissociated using standard techniques such as digestion with a collagenase, trypsin or other protease solution and are then seeded into the mold or polymer scaffold immediately or after being maintained in culture. Cells can be normal or genetically engineered to provide additional or normal function. Immunologically inert cells, such as embryonic or fetal cells, stem cells, and cells genetically engineered to avoid the need for immunosuppression can also be used. Methods and drugs for immunosuppression are known to those skilled in the art of transplantation.

Undifferentiated or partially differentiated precursor cells, such as embryonic gel axe cells (Gearhart, et al., U.S. Pat. No. 6,245,566), embryonic stem cells (Thomson, U.S. Pat. Nos. 5,843,780 and 6,200,802), mesenchymal stem cells (Caplan, et al. U.S. Pat. No. 5,486,359), neural stem cells (Anderson, et al., U.S. Pat. No. 5,849,553), hematopoietic stem cells (Tsukarnoto, U.S. Pat. No. 5,061,620), multipotent adult stem cells (Furcht, et al., WO 01/11011) can be used in this invention. Cells can be kept in an undifferentiated state by co-culture with a fibroblast feeder layer (Thomson, U.S. Pat. Nos. 5,843,780 and 6,200,802), or by feeder-free culture with fibroblast conditioned media (Xu, et al. Nat. Biotechnol., 19, 971 (2001)). Undifferentiated or partially differentiated precursor cells can be induced down a particular developmental pathway by culture in medium containing growth factors or other cell-type specific induction factors or agents known in the art. Some examples of such factors are shown in Table 1.

TABLE 1

Selected Examples of Differentiation Inducing Agents

| Agent | Progenitor | Differentiated Cell |
| --- | --- | --- |
| Vascular Endothelial Growth Factor | Embryonic Stem Cell | Hematopoietic Cell[1] |
| Sonic Hedgehog | Floor Plate | Motor Neuron[2] |
| Insulin-like Growth Factor II | Embryonic Stem Cell | Myoblast[3] |
| Osteogenin | Osteoprogenitor | Osteoblast[4] |
| Cytotoxic T Cell Differentiation Factor | Spleen Cell | Cytotoxic T Lymphocyte[5] |
| β-catenin | Skin Stem Cell | Follicular Keratinocyte[6] |
| Bone Morphogenic Protein 2 | Mesenchymal Stem Cell | Adipocytes, Osteoblasts[7] |
| Interleukin 2 | Bone Marrow Precursor | Natural Killer Cells[8] |
| Transforming Growth Factor β | Cardiac Fibroblast | Cardiac Myocyte[9] |
| Nerve Growth Factor | Chromaffin Cell | Sympathetic Neuron[10] |
| Steel Factor | Neural Crest | Melanocyte[11] |

TABLE 1-continued

Selected Examples of Differentiation Inducing Agents

| Agent | Progenitor | Differentiated Cell |
|---|---|---|
| Interleukin 1 | Mesencephalic Progenitor | Dopaminergic Neuron[12] |
| Fibroblast Growth Factor 2 | GHFT | Lactotrope[13] |
| Retinoic Acid | Promyelocytic Leukemia | Granulocyte[14] |
| Wnt3 | Embryonic Stem Cell | Hematopoietic Cell[15] |

[1]Keller, et al. (1999) *Exp. Hematal* 27: 777-787.
[2]Marti, et al. (1995) *Nature.* 375: 322-325.
[3]Prelle, et al. (2000) *Biochem. Biophy. Res. Commun.* 277: 631-638.
[4]Amedee, et al. (1994) *Differentiation.* 58: 157-164.
[5]Hardt, et al. (1985) *Eur. J. Immunol.* 15: 472-478.
[6]Huelsken et al. (2001) *Cell.* 105: 533-545.
[7]Ji, et al. (2000) *J. Bone Miner. Metab.* 18: 132-139.
[8]Migliorati, et al. (1987) *J. Immunol.* 138: 3618-3625.
[9]Eghbali, et al. (1991) *Prob. Natl. Acad. Sci. USA.* 88: 795-799.
[10]Niijima, et al. (1995) *J. Neurosci.* 15: 1180-1194.
[11]Guo, et al. (1997) *Dev. Biol.* 184: 61-69.
[12]Ling, et al. (1998) *Exp. Neurol.* 149: 411-423.
[13]Lopez-Fernandez, et al. (2000) *J. Biol. Chem.* 275: 21653-60.
[14]Wang, et al. (1989) *Leuk. Res.* 13: 1091-1097.
[15]Lako, et al. (2001) *Mech. Dev.* 103: 49-59.

A stem cell can be any known in the art, including, but not limited to, embryonic stem cells, adult stem cells, neural stem cells, muscle stem cells, hematopoietic stem cells, mesenchymal stem cells, peripheral blood stem cells and cardiac stem cells. Preferably, the stem cell is human. A "stem cell" is a pluripotent, multipotent or totipotent cell that can undergo self-renewing cell division to give rise to phenotypically and genotypically identical daughter cells for an indefinite time and can ultimately differentiate into at least one final cell type.

The quintessential stem cell is the embryonal stem cell (ES), as it has unlimited self-renewal and multipotent and or pluripotent differentiation potential, thus possessing the capability of developing into any organ, tissue type or cell type. These cells can be derived from the inner cell mass of the blastocyst, or can be derived from the primordial germ cells from a post-implantation embryo (embryonal germ cells or EG cells). ES and EG cells have been derived from mice, and more recently also from non-human primates and humans. Evans et al. (1981) Nature 292:154-156; Matsui et al. (1991) Nature 353:750-2; Thomson et al. (1995) Proc. Natl. Acad. Sci. USA. 92:7844-8; Thomson et al. (1998) Science 282:1145-1147; and Shamblott et al. (1998) Proc. Natl. Acad. Sci. USA 95:13726-31.

The terms "stem cells," "embryonic stem cells," "adult stem cells," "progenitor cells" and "progenitor cell populations" are to be understood as meaning in accordance with the present invention cells that can be derived from any source of adult tissue or organ and can replicate as undifferentiated or lineage committed cells and have the potential to differentiate into at least one, preferably multiple, cell lineages.

The hepatocytes added to the apparatus of the invention can be highly proliferative hepatocytes, known as small hepatocytes (SHCs), which have the ability to proliferate in vitro for long periods of time (Mitaka, et al., Biochem Biophys Res Commun 214, 310 (1995); Taneto, et al, Am J Pathol 148, 383 (1996)). Small hepatocytes express hepatocyte specific functions such as albumin production (Mitalca, et al., Hepatology 29, 111 (1999)). The survival and function of small hepatocytes when co-cultured on three-dimensional micronorous biodegradable polymer molds under dynamic culture conditions was demonstrated (Example 4).

Methods for Seeding Cells into Molds or Polymer Scaffolds
Cell Seeding

After the mold with the desired high degree of micromachining is prepared, the molds themselves or polymer scaffolds are seeded with the desired cells or sets of cells. The distribution of cells throughout the mold or polymer scaffold can influence both (1) the development of a vascularized network, and (2) the successful integration of the vascular device with the host. The approach used in this invention is to provide a mechanism for the ordered distribution of cells onto the mold or polymer scaffold. Cells that are enriched for extracellular matrix molecules or for peptides that enhance cell adhesion can be used. Cells can be seeded onto the mold or polymer scaffold in an ordered manner using methods known in the art, for example, Teebken, et al., Eur J. Vasa Endovasc. Surg. 19, 381 (2000); Ranucci, et al., Biomaterials 21, 783 (2000). Also, tissue-engineered devices can be improved by seeding cells throughout the polymeric scaffolds and allowing the cells to proliferate in vitro for a predetermined amount of time before implantation, using the methods of Burg et al., J. Biomed. Mater. Res 51, 642 (2000).

For purposes of this invention, "animal cells" can comprise endothelial cells, parenchymal cells, bone marrow cells, hematopoietic cells, muscle cells, osteoblasts, stem cells, mesenchymal cells, stem cells, embryonic stem cells, or fibroblasts. Parenchymal cells can be derived from any organ, including heart, liver, pancreas, intestine, brain, kidney, reproductive tissue, lung, muscle, bone marrow or stem cells.

In one embodiment, the mold or polymer scaffold is first seeded with a layer of parenchymal cells, such as hepatocytes or proximal tubule cells. This layer can be maintained in culture for a week or so in order to obtain a population doubling. It can be maintained in a perfusion bioreactor to ensure adequate oxygen supply to the cells in the interior. The apparatus is then seeded with a layer of endothelial cells and cultured further. In regions where the matrix is resorbed rapidly, the tissue can expand and become permeated with capillaries.

Cell Seeding of Horizontal Layer by Laminar Flow.

A structure comprising joined or fastened molds and/or polymer scaffolds, with or without a semi-permeable membrane between them, is called an "apparatus" for purposes of this invention. Sets of cells can be added to or seeded into the three-dimensional apparatuses, which can serve as a template for cell adhesion and growth by the added or seeded cells. The added or seeded cells can be parenchymal cells, such as hepatocytes or proximal tubule cells. Stem cells can also be used. A second set of cells, such as endothelial cells, can be added to or seeded onto the assembled apparatus through other vessels than those used to seed the first set of cells. The cell seeding is performed by slow flow. As a practical matter, the geometry of the apparatus will determine the flow rates. In general, endothelial cells can enter and form vessel walls in micromachined channels that are about 10-50 µm. Thus, in addition to serving as a mechanical framework for the organ, the assembled apparatus provides a template for all of the microstructural complexity of the organ, so that cells have a mechanical map to locate themselves and form subsystems, such as blood vessels in the liver.

Optionally, functional cells are seeded into both a first and second mold and/or polymer scaffold with microchannels on their surfaces, and the two molds and/or polymer scaffolds are joined or fastened with a semi-permeable membrane between them, allowing gas exchange, diffusion of nutrients, and waste removal. One layer comprises the circulation through which blood, plasma or media with appropriate levels of oxygen can be continuously circulated to nourish the second layer. The second layer comprises a reservoir for the functional cells of an organ, and optionally includes inlets for neural inervation, urine flow, biliary excretion or other activity. This results in an apparatus for making tissue lamina, wherein each of the first and second molds and/or polymer scaffolds and the semi-permeable membrane are comprised of material that is suitable for attachment and culturing of animal cells. The sheet of tissue created by the apparatuses and/or methods of the invention is referred to as "tissue lamina".

Figure 11:
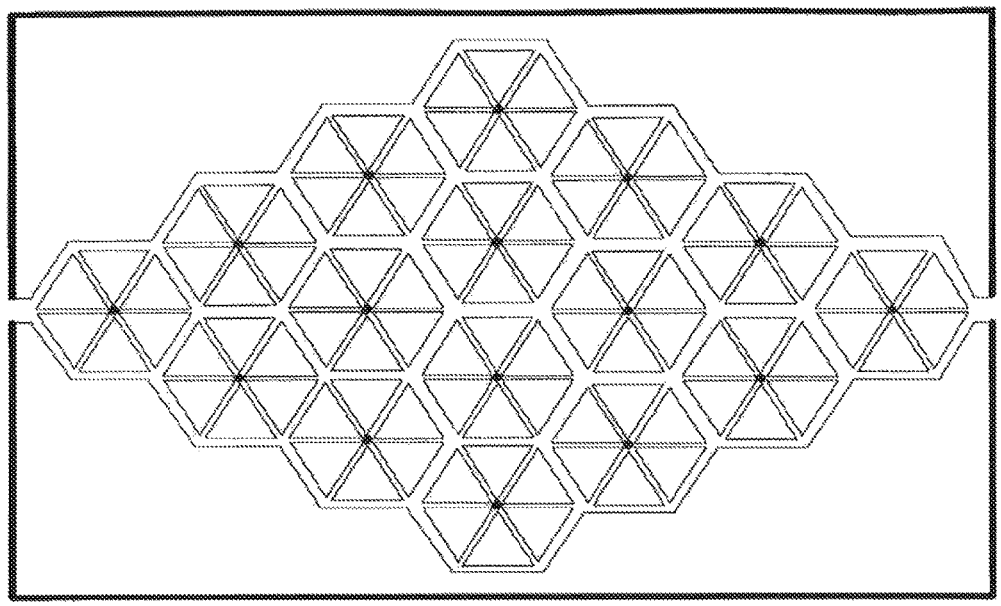
FIG. 11 shows a schematic top drawing of a mold or polymer scaffold. The triangles represent areas coated with cell adhesion molecules to promote the adhesion of cells (e.g. hepatocytes). The white areas between the triangles represent microchannels; in some applications, they are not coated with cell adhesion molecules, and so are open for colonization by cells that can form vascular tissue (e.g. endothelial cells). The black circle in the middle of each hexagon is a vertical through-hole.

Channels in the horizontal direction typically proceed from larger to smaller to larger. The geometries can be as complex as desired in-plane (horizontal direction). Thus, one can use small geometries in-plane (such as horizontal conduits of about 5-20 µm). The alignment of through-holes creates vertical conduits or channels in the z-axis. However, the vertical channels need not go from larger to smaller to larger. In the vertical direction, the vertical channels are typically parallel to each other and have diameters on the micron level, large enough only to allow cell seeding (e.g., hepatocytes are about 40 µm). In one embodiment, different types of cells are seeded horizontally onto different layers of the assembled apparatus. In another embodiment, the different types of cells are seeded using pores or channels from different directions. Various combinations are also possible. (See FIG. 11.)

Although described herein with particular reference to formation of vascularized tissue, it should be understood that the channels can be used to form lumens for passage of a variety of different fluids, not just blood, but also bile, lymph, nerves, urine, and other body fluids, and for the guided regeneration or growth of other types of cells, especially nerve cells. The tissue layer can include some lumens for forming vasculature and some for other purposes, or be for one purpose, typically providing a blood supply to carry oxygen and nutrients to and from the cells in the tissue.

Molecules such as growth factors or hormones can be covalently attached to the surface of the molds and/or polymer scaffolds and/or semi-permeable membrane to effect growth, division, differentiation or maturation of cells cultured thereon.

Construction of Tissue or Organ Equivalents

Figure 13:
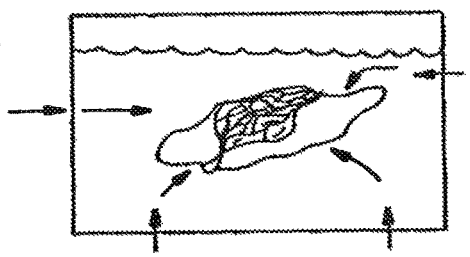
FIG. 13 shows a schematic of an assembled complex tissue or organ formed by the process of FIG. 8.

Engineered tissue lamina can be systematically folded and compacted into a three-dimensional vascularized structure, as shown in FIGS. 12 and 13. The two-dimensional surface of the mold can be varied to aid in the folding and compacting process. For example, the surface can be changed from planar to folded accordion-like. It can be stacked into multiple converging plates. It could be curvilinear or have multiple projections.

Different types of tissue, or multiple layers of the same type of tissue, can be superposed prior to folding and compacting, to create more complex or larger structures. For example, a tubular system can be layered onto a vascular system to fabricate glomerular tissue and collecting tubules for kidneys. Bile duct tubes can be overlaid on vascularized liver or hepatocyte tissue, to generate a bile duct drainage system. Alveolar or airway tissue can be placed on lung capillaries to make new lung tissue. Nerves or lymphatics can be added using variations of these same general techniques.

FIGS. 12A-G are perspective views of ways in which a single tissue lamina (FIG. 12A) can be folded (FIGS. 12B and 12C) or stacked (FIG. 12D), or expanded to form a balloon shape (FIG. 12E), funnel (FIG. 12F), or large lumen (FIG. 12G).

Figure 9B:
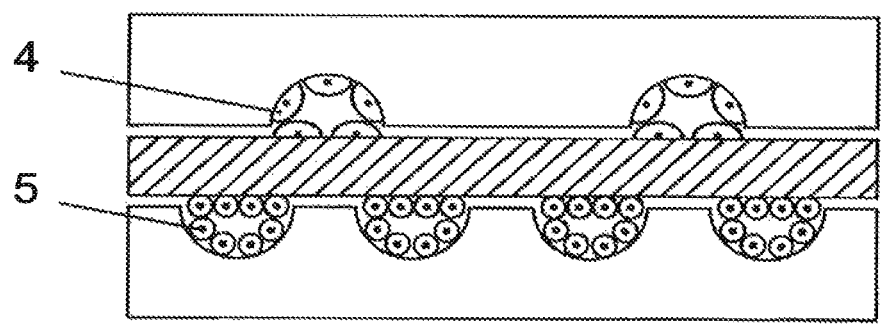

In addition to embodiments in which a single tissue layer is formed, the apparatus shown in FIG. 9 can be used for three dimensional tissue and organ formation. The addition of the second mold or polymer scaffold allows the functional unit of the organ to be added, and likewise allows precision for patterning of exocrine outflow. For example, in the liver, the parenchymal cells are hepatocytes and the exocrine system is the biliary system. By the addition of the second compartment containing hepatocyes and biliary cells, the functional tissue of the liver can be achieved and biliary excretion can be designed and enfolded.

This patterning can be made more complex with the addition of further layers separated by permeable membranes. Several molds and/or polymer scaffolds, with or without semi-permeable membranes between them, can be stacked in rational arrays to produce complex tissue in 3-dimensional space (see FIG. 28, for example). These layers of molds and/or polymer scaffolds, and optionally, semi-permeable membranes, can be appropriately interdigitated and connected (e.g. via through-holes) to produce vascular connections through the depths of the stack, as well as excretory outflow systems through the depths of the tracts.

Stacking Molds and/or Polymer Scaffolds to Achieve Three Dimensionality.

Extension of the two-dimensional technology into the third dimension can be accomplished by stacking the two-dimensional layers on top of each other. This stacking method begins with many molds and/or polymer scaffolds produced by the techniques described in previous sections. Once these molds and/or polymer scaffolds (nominally of the same size) are created, they are lain down or bonded to other separate molds and/or polymer scaffolds, atop one another. The layers can be connected by through-holes, which extend through the z-axis of the molds and/or polymer scaffolds. The pattern of microchannels on the surface of each mold or polymer scaffold can differ or be similar to the previous layer, depending upon fluid mechanical considerations. In addition to the two-dimensional channels embedded in each layer, the through-holes can provide vessel structures that extend up into the third (vertical) dimension. Each successive layer could have slightly different patterns of through-holes, on that the effect would be to have vessels extending into the third dimension that are not necessarily precisely perpendicular to the plane of the sheet.

By extending this technology as needed, one can move from the presently achievable formation of small (~100 cm$^2$) tissue sheets, each containing one plane of blood vessels, to the formation of perhaps 100 cm$^3$ of material, enough to build an organ. The process is low-cost, scalable, can be customized for the physiology of a particular patient, and is based upon currently available microfabrication technology.

Fastening the Stacked Layers.

An aspect of this invention is the fastening or sealing of the polymeric mold layers. Preferably, the layers are irreversibly bound before implantation into the host. Depending on the composition of the layered material, the layers can be sealed by solvent bonding; reflow by heating (40° C.); treating surface with oxygen plasma; or by polymer flow at the surface. Biocompatible polymer materials maybe bonded together by plasma activation to form sealed structures (Jo et al., SPIE 3877, 222 (1999)). The basic process results in bonded layers with channel architecture closely resembling that obtained with silicon etched molds.

Silicon-Glass Microfluidic Chambers to Test Sealing of Stacks.

Microfluidic tests have been performed that demonstrate that bonded apparatuses are leakproof and support fluid pressures necessary for dynamic cell seeding. (See Example 3.) One of the most common methods used to seal micromachined wafers together is anodic bonding, a technique based on the high concentration of mobile ions in many glasses (Camporese, et al., IEEE Electron. Device Lett. EDL 2, 61(1981)). This process produces a permanent seal; fracture testing of silicon-glass anodically bonded interfaces produces a failure within the bulk of the glass.

Etched wafers maybe bonded together, producing closed lumens suitable for fluidic experiments. A fluidic test was performed with a mixed-phase flow of alcohol with 10 μm fluorescent microspheres. An unetched glass capping layer was mechanically drilled for inlet and outlet fluid ports, and then anodic ally bonded to a silicon wafer plasma-etched with the TEP-1-geometry. A permanent seal with no leaks was produced, enabling one to obtain highly accurate pressure and flow data.

Alternatively, the multilayer device of the invention can be configured such that each of the layers has an alignment indentation on one surface of the layer and an alignment protrusion on the opposing surface of another layer. The alignment indentations shaped to mate with the alignment protrusion, so that the layers are held together.

Alternative Methods of Stacking.

To build up the mold and/or polymer scaffold layers by mechanical assembly, the layers can be mechanically mated using biodegradable or non-biodegradable barbs, pins, screws, clamps, staples, wires, string, or sutures. (See, U.S. Pat. No. 6,143,293.) With this mechanical assembly approach, each prefabricated section can comprise different mold and/or polymer scaffold material and/or different mold microstructures. Different sections of these can be seeded with cells before assembly. Cells thus be can be embedded into the mold or polymer scaffold by assembling sections around these components. In addition, surface features on each mold, which are readily fabricated, become part of the internal microstructure (e.g., molded surface channels become conduits for cell infusion, or for blood flow to stimulate angiogenesis). A surface feature on an individual mold or polymer scaffold will become an internal feature when another segment is assembled over it. For example, surface features such as channels can be micromachined into a first mold or polymer scaffold layer. When a second mold or polymer scaffold layer is placed atop that a first layer, the micromachined surface feature becomes an internal feature of the apparatus.

Rolling or Folding to Achieve Three Dimensionality

An alternate method for achieving three-dimensionality is to generate a long strip of polymer mold material, which contains repeating units of the blood vessel network along with through-holes, and to fold the mold film in a z-fold fashion while aligning the through-holes to one another.

The rolling or folding process begins with the generation of a lengthy strip of polymer mold material, which contains a serial array of unit cells each of which is comprised of an array of channels mimicking the vascular network, produced from a wafer mold by molding, embossing, or the like. These unit cells can be identical or can be different. The units are linked to through-holes that provide the vertical channel connections between horizontal blood vessel layers. Once the polymeric scaffold strip has been formed, it is folded in a z-fold fashion (FIG. 12C), and bonded together so that each fold is attached to the film portions above and below it with alignment to the through-holes.

This roll can be of a length to provide sufficient scaffolding material for an entire human organ, which can be hundreds or even more multiples of the area of a single wafer. Each section of the roll is a sheet of polymeric mold with closed lumens, or vessels. The vessels in each folded section of sheet are connected to a through-hole at the edge of the sheet (for example, one on each side, for inlet and outlet blood flow). During folding, the sheet sections are folded such that the through-hole openings align, forming a vessel in the third (z) dimension.

The roll can be in the shape of a spiral, helix, jelly roll or other cylindrically shaped objects. (See FIG. 12.)

Figure 14:
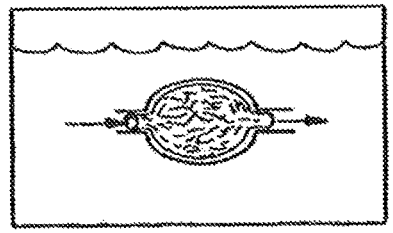
FIG. 14 shows how the organ of FIG. 5 can be connected to a fluid by anastomosis of the inlet and outlet.

The described three-dimensional tissue structures can then be imp/anted into animals or patients by directly connecting the blood vessels to flow into and out of the apparatus, as depicted in FIG. 14. Immediate perfusion of oxygenated blood occurs, which allows survival and function of the entire living mass.

In a one embodiment, tissue-engineered liver is formed. Preferably, tissue engineered liver comprises both functioning hepatocytes and bile ducts. (See FIG. 9B.) The biliary system of native liver begins with a minute hexagonal bile canaliculus, which is formed from specialization of the adjacent surfaces of individual hepatocytes, which are sealed with tight junctions. These canaliculi are confluent with terminal biliary ductules, which are initially made of squamous cells, but give way to low cubiodal biliary epithelium as they approach the interlobular bile ducts. One liter of bile per day is secreted by hepatocytes and moved out of the liver through this system. There have been previous reports of the formation of duct-like structures in a variety of long-term in vitro and in vivo hepatocyte cultures (Block, et al., J Cell Biol, 132, 1133 (1996); Landry, et al., J Cell Biol, 101, 914 (1985); Mitaka, et al., Hepatology 29, 111 (1999); Nishikawa, et al., Exp Cell Res, 223, 357 (1996); Uyama, et al., Transplantation 55, 932 (1993)). In Example 4, engineered liver tissue, cultured in microfabricated channels of a single layer mold, is shown to comprise structures resembling bile ducts.

In a yet another embodiment, tissue-engineered kidney is formed. Preferably, tissue engineered kidney comprises functioning proximal tubules. Tissue-engineered kidney functions as a native kidney; glomerular ultrafiltrate flows from the glomerular endothelium and passes through a semipermeable membrane into a proximal tubule network where reabsorption occurs (see Example 5).

Extracomoreal Support Devices

The invention can be adapted to comprise devices for uses in addition to the formation of implantable tissue. Such devices can be extracorporeal, and may provide partial support function, may extend the time between hospital treatments for patients on chronic organ support therapies, and will improve the quality of life between hospital treatments. Current extracorporeal devices known in the art do not incorporate the precise microfabrication capabilities offered by MEMS technology, and therefore function is limited by the resolution limits of current hollow fiber and membrane fabrication methods. Insertion of MEMS technology into this domain is expected to have major benefits for hemofiltering, dialysis and other applications. For example, the designs can be adapted to produce an extracorporeal renal dialysis device, an extracorporeal liver device, or an extracorporeal artificial lung device. Such devices may or may not be supported with living cells loaded or seeded into the device.

The systems of the invention can be implanted into a subject to supplement or replace the biological function of a tissue or organ. Alternatively, the systems can remain ex viva, serving as extracorporeal devices to supplement or replace biological function. As used herein, the term "biological function" refers to the structural, mechanical or metabolic activity of a tissue or organ. Extracorporeal devices of the present invention can comprise hybrid devices suitable for both ex vivo and in vivo use.

The Examples presented herein demonstrate that microfabrication technology can be adapted to suit the needs of all living tissues. An important aspect of the present invention lies in its control of form over extremely small distances. The resolution of the microfabrication techniques is on the order of about 0.1 µm from point to point. This level of precision adds new levels of control in the ability to design and guide new tissue formation. For instance, surfaces can be imprinted with submicron grooves or scallops, and corners can be made rounded, angled or sharp with this same level of submicron precision. Geometric control at this scale can have a powerful impact on cell adhesion through mechanisms such as contact guidance, as described by Den Braber, et al. J. Biomed. Mater. Res. 40, 291 (1998).

The following Examples are provided to illustrate the invention, and should not be considered to limit its scope in any way.

EXAMPLE 1

Micromaching of Template to Tissue Engineer Branched Vascularized Channels for Liver Fabrication Micromaching technologies were used on silicon and pyrex surfaces to generate complete vascular systems that can be integrated with engineered tissue before implantation. Trench patterns reminiscent of branched architecture of vascular and capillary networks were etched using standard photolithographic techniques onto silicon and pyrex surfaces to serve as templates. Hepatocytes and endothelial cells were cultured and subsequently lifted as single-cell monolayers from these two dimensional molds. Both cell types were viable and proliferative on these surfaces. In addition, hepatocytes maintained albumin production. The lifted monolayers were then folded into compact three-dimensional tissues. The goal is to lift these branched vascular networks from two-dimensional templates so that they can be combined with layers of parenchymal tissue, such as hepatocytes, to form three-dimensional conformations of living vascularized tissue for implantation.

Materials and Methods

Micromachining Techniques

Templates for the formation of sheets of living vascularized tissue were fabricated utilizing micromachining technology. For the present work, a single level etch was utilized to transfer a vascular network pattern into an array of connected trenches in the surface of both silicon and pyrex wafers.

In this prototype, a simple geometry was selected for patterning the vascular network. Near the edge of each wafer, a single inlet or outlet was positioned, with a width of 500 µm. After a short length, the inlet and outlet branched into three smaller channels of width 250 µm; each of these branched again into three 125 µchannels, and finally down to three 50 µn channels. Channels extend from the 50 µm channels to form a capillary network, which comprises the bulk of the layout. In between these inlet and outlet networks lies a tiled pattern of diamonds and hexagons forming a capillary bed and filling the entire space between the inlet and outlet. In one configuration, the capillary width was set at 25 µm, while in the other, capillaries were fixed at 10 µm. This geometry was selected because of its simplicity as well as its rough approximation to the size scales of the branching architecture of the liver. Layout of this network was accomplished using CADENCE software (Cadence, Chelmsford, Mass.) on a Silicon Graphics workstation. A file with the layout was generated and sent electronically to Align-Rite (Burbank, Calif.), where glass plates with electron-beam-generated patterns replicating the layout geometry were produced and returned for lithographic processing.

Starting materials for tissue engineering template fabrication were standard semiconductor grade silicon wafers (Virginia Semiconductor, Powhatan, Va.), and standard pyrex wafers (Bullen Ultrasonics, Eaton, Ohio) suitable for MEMS processing. Silicon wafers were 100 mm diameter and 525 µm thick, with primary and secondary flats cut into the wafers to signal crystal orientation. Crystal orientation was <100>, and wafers were doped with boron to a resistivity of approximately 5 W-cm. The front surface was polished to an optical finish and the back surface ground to a matte finish. Pyrex wafers were of composition identical to Corning 7740 (Corning Glass Works, Corning N.Y.), and were also 100 mm in diameter, but had a thickness of 775 µm. Both front and back surfaces were polished to an optical finish. Prior to micromachining, both wafer types were cleaned in a mixture of 1 part $H_2SO_4$ to 1 part $H_2O_2$ for 20 minutes at 140° C., rinsed 8 times in deionized water with a resistivity of 18 MW, and dried in a stream of hot $N_2$ gas.

For silicon and pyrex wafers, standard photolithography was employed as the etch mask for trench formation. Etching of pyrex wafers requires deposition of an intermediate layer for pattern transfer which is impervious to the etch chemistry. A layer of polysilicon of thickness 0.65 µm over the pyrex was utilized for this purpose. This layer was deposited using Low Pressure Chemical Vapor Deposition (LPCVD) at 570° C. and 500 mTorr via the standard silane decomposition method. In the case of silicon, photoresist alone could withstand limited exposure to two of the three etch chemistries employed. For the third chemistry, a 1.0 µm layer of silicon dioxide was thermally deposited at 1100° C. in hydrogen and oxygen.

Once the wafers were cleaned and prepared for processing, images of the prototype branching architecture were translated onto the wafer surfaces using standard MEMS lithographic techniques. A single layer of photoresist (Shipley 1822, MicroChem Corp., Newton, Mass.) was spun onto the wafer surfaces at 4000 rpm, providing a film thickness of approximately 2.4 µm. After baking at 90° C. for 30 minutes, the layer of photoresist was exposed to uv light using a Karl Russ MA6 (Suss America, Waterbury, Vt.) mask aligner. Light was passed through the lithographic plate described earlier, which was in physical contact with the coated wafer. This method replicates the pattern on the plate to an accuracy of 0.1 µm. Following exposure, wafers were developed in Shipley 319 Developer (MicroChem Corp., Newton, Mass.), and rinsed and dried in deionized water. Finally, wafers were baked at 110° C. for 30 minutes to harden the resist, and exposed to an oxygen plasma with 80 Watts of power for 42 seconds to remove traces of resist from open areas.

Silicon wafers were etched using three different chemistries, while pyrex wafers were processed using only one technique. For pyrex, the lithographic pattern applied to the polysilicon intermediate layer was transferred using a brief (approximately 1 minute) exposure to $SF_6$ in a reactive-ion-etching plasma system (Surface Technology Systems, Newport, United Kingdom). Photoresist was removed, and the pattern imprinted into the polysilicon layer was transferred into trenches in the silicon using a mixture of 2 parts $HNO_3$ to 1 part HF at room temperature. With an etch rate of 1.7 µm per minute, 20 µm deep trenches were etched into the pyrex wafers in approximately 12 minutes. Since the chemistry is isotropic, as the trenches are etched they become wider. Processing with the layout pattern with 25 µm wide capillary trenches tended to result in merging of the channels, while the use of 10 µm wide trenches avoided this phenomenon. Interferometric analysis of the channels after etching showed that surface roughness was less than 0.25 µm. Once channel etching of pyrex wafers was completed, polysilicon was removed with a mixture of 10 parts $HNO_3$ to 1 part HF at room temperature, and wafers were recleaned in 1 part $H_3SO_4$ to 1 part HF.

Three different chemistries were employed to etch silicon in order to investigate the interaction between channel geometry and cell behavior. First, a standard anisotropic plasma etch chemistry, using a mixture of $SF_6$ and $C4F_8$ in a switched process plasma system from STS[24], was used to produce rectangular trenches in silicon. Narrower trenches are shallower than deep trenches due to a phenomenon known as RIE lag. A second process utilized a different plasma system from STS, which produces isotropic trenches with a U-shaped profile. While the process is isotropic, widening of the trenches is not as severe as is experienced in the isotropic pyrex etching process described earlier. In both of these plasma etching cases, trenches were etched to a nominal depth of 20 µm. For the third process, anisotropic etching in KOH (45% w/w in $H_2O$ at 88° C.), the intermediate silicon dioxide layer mentioned above was employed. First, the silicon dioxide layer was patterned using HF etching at room temperature. The KOH process produces angled sidewalls rather than the rectangular profile or U-shaped profile produced by the first two recipes, respectively. Crystal planes in the <111> orientation are revealed along the angled sidewalls, due to anisotropic properties of the KOH etch process as a function of crystal orientation. Due to the self-limiting nature of the channels produced by this process, trench depth was limited to 10 µm. After completion of the silicon wafer etching, all layers of photoresist and silicon dioxide were removed, and wafers were cleaned in 1 part $H_2SO_4$:1 part $H_2O_2$ at 140° C., followed by rinsing in deionized water and drying in nitrogen gas.

For this set of experiments, no attempt was made to alter the surface chemistry of the silicon and pyrex wafers. Prior to processing, silicon wafers were uniformly hydrophobic, while pyrex wafers were equally hydrophilic, as determined by observations of liquid sheeting and sessile drop formation. After processing, unetched surfaces appeared to retain these characteristics, but the surface chemistry within the channels was not determined.

Animals

Adult male Lewis rats (Charles River Laboratories, Wilmington, Mass.), weighing 150-200 g, were used as cell donors. Animals were housed in the Animal Facility of Massachusetts General Hospital in accordance with guide lines for the care of laboratory animals. They were allowed rat chow and water ad libitum and maintained in 12-hour light and dark cycle.

Cell Isolations

Male Lewis rats were used as hepatic cell donors. HCs were isolated using a modification of the two-step collagenase perfusion procedure as previously described by Aiken, et al., J Pediatr Surg 25, 140 (1990) and Seglen, Methods Cell Biol 13, 29 (1976). Briefly, the animals were anesthetized with Nembutal Sodium Solution (Abbott Laboratories, North Chicago, Ill.), 50 mg/kg, and the abdomen was prepared in sterile fashion. A midline abdominal incision was made and the infrahepatic inferior vena cava was cannulated with a 16-gauge angiocatheter (Becton Dickinson), The portal vein was incised to allow retrograde efflux and the suprahepatic inferior vena cava was ligated. The perfusion was performed at a flow rate of 29 ml/min initially with a calcium-free buffer solution for 5 to 6 minutes, then with a buffer containing collagenase type 2 (Worthington Biomedical Corp., Freehold, N.J.) at 37° C. The liver was excised after adequate digestion of the extracellular matrix and mechanically agitated in William's E medium (Sigma, St. Louis, Mo.) with supplements to produce a single cell suspension. The suspension was filtered through a 300 µm mesh and separated into two fractions by centrifugation at 50 g for 2 minutes at 4° C. The pellet containing the viable HC fraction was resuspended in William's E medium and further purified by an isodensity Pereoll centrifugation. The resulting pellet was then resuspended in Hepatocyte Growth Medium, and cell counts and viabilities of HCs were determined using the trypan blue exclusion test.

The endothelial cells were derived from rat lung microvessels and they were purchased directly from the vendor, Vascular Endothelial Cell Technologies (Rensellaer, N.Y.).

Hepatocyte Culture Medium

William's E medium supplemented with 1 g sodium pyruvate (Sigma, St. Louis, Mo.) and 1% glutamine-penicillin-streptomycin (Gibco BRL, Gaithersburg, Md.) were used during the cell isolation process. The plating medium was Dulbecco's modified eagle medium (Gibco BRL) supplemented with 10% fetal bovine serum, 1% penicillin-streptomycin, 44 mM sodium-bicarbonate, 20 mM HEPES, 10 mM niacinamide, 30 microgram/nil L-proline, 1 mM ascorbic acid 2 phospate, 0.1 µM dexamethasone (Sigma), insulin-transferrin-sodium selenite (5 mg/L-5 mg/L-5 µgram/L, Roche Molecular Biomedicals, Indianapolis, Ind.), and 20 rig/mL epidermal growth factor (Collaborative Biomedical Products, Bedford, Mass.).

Endothelial Cell Culture Medium

Dulbecco's modified eagle medium (Gibco BRL) was supplemented with 10% fetal bovine serum, 1% penicillin-streptomycin, 25 mg of ascorbic acid (Sigma), 10 mg L-alanine (Sigma), 25 mg L-proline (Sigma), 1.5 microgram cupric sulfate (Sigma), glycine (Sigma) and 1M Hepes buffer solution (Gibco BRL). The media was supplemented with 8 mg of ascorbic acid every day.

Cell Attachment and Lifting from Non-Etched Silicon and Pyrex Wafers

Silicon and pyrex were both tested as possible substrates for the culture and lifting of endothelial cells and hepatocytes. Prior to cell seeding, the pyrex wafers were sterilized with 70% ethanol (Fisher, Pittsburgh, Pa.) overnight and washed three times with sterile phosphate buffered saline (Gibco BRL). Silicon wafers were first soaked in acetone for 1 hr, followed a methanol rinse for 15 minutes, and overnight sterilization in 100% isopropyl alcohol. Rat lung microvascular endothelial cells was cultured on non-coated pyrex and silicon surfaces, as well as wafers coated with vitrogen (30 microgram/ml), Matrigel® (1%), or Gelatin (10 mg/ml). Once isolated, the cells were resuspended in endothelial cell culture medium, seeded uniformly onto the wafer at a density of $26.7 \times 10^3$ cells/cm$^2$, and cultured at 5% $CO_2$ and 37° C. After reaching confluence, the ability of the monolayer of endothelial cells to lift from the wafers was tested using a cell scrapper to promote detachment.

The rat hepatocytes were also cultured on non-coated pyrex and silicon, as well as wafers coated with a thin and thick layers of vitrogen (30 microgram/ml and 3 microgram/ml) and Matrigel (1%) in order to determine the optimal methods for lifting hepatocyte sheets. Once isolated, the hepatocytes were resuspended in hepatocyte growth media, seeded onto the wafer at a density of $111.3 \times 10^3$ cells/cm$^2$, and cultured at 5% $CO_2$ and 37° C. Cell attachment and growth was observed daily using microscopy and cell lifting occurred spontaneously.

After determining which method for culturing was best for lifting the hepatocytes and endothelial cells in an intact layer, both membranes were fixed in 10% buffered formalin for 1 hr and harvested for histological study, and the hepatocytes were stained immunohistochemically.

Immunohistochemical Staining

The hepatocyte cell monolayer membrane was fixed in 10% buffered formalin and processed for hematoxylin-eosin and immunohistochemical staining using a labeled streptavidin biotin method (LSAB2 kit for rat specimen, DAKO, Carpinteria, Calif.). The primary antibody was rabbit anti-albumin (ICN, Costa Mesa, Calif.). Three-micron sections were prepared and deparafinized. The specimens were treated with peroxidase blocking buffer (DAKO) to prevent the nonspecific staining. Sections were stained with albumin diluted with phosphate buffered saline, followed by biotinylated anti-rabbit antibody and HRP conjugated streptavidin. Sections were treated with DAB as substrate and were counterstained with hematoxylin.

Albumin Production

Figure 15:
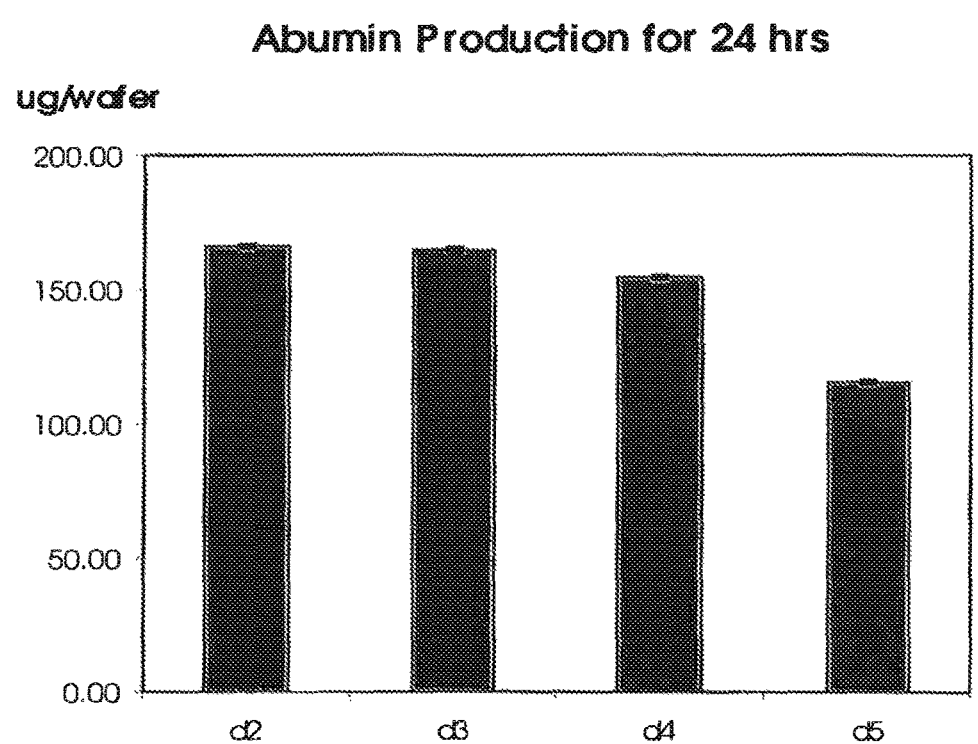
FIG. 15 shows a set of bar graphs demonstrating continued albumin production by hepatocyte cells cultured in a polymer scaffold of the invention. Albumin concentration in culture medium was measured every 24 hours for 5 days pre-cell detachment using an enzyme linked immunosorbent assay. No significant differences were observed between day 2, day 3, and day 4 (p<0.05 by the paired t-test).

To assess hepatocyte function, albumin concentration in the culture medium was measured every 24 hours for 5 days pre-cell detachment using an enzyme linked immunosorbent assay (n=5), as described by Schwere, et al., Clinica Chernica Acta 163, 237 (1987). In brief, a 96 well microplate was coated with anti-rat albumin antibody (ICN). After blocking non-specific responses with a 1% gelatin solution, each sample was seeded onto the plate and incubated for 1 hour at 37° C. This was followed by another 1 hour incubation with peroxidase conjugated anti-rat albumin antibody (ICN). Finally, the substrate was added and extinction was measured with a microplate reader at 410 nm. $R^2$ of the standard curve was >0.99. Results demonstrate continued production of albumin by cultured hepatocytes (FIG. 15).

Statistical Analysis

All data was expressed as mean+/−SD. Statistical analysis was performed with a paired t-test. Statistical significance was determined as when the p value of each test was less than 0.05.

Cell Attachment to Etched Silicon and Pyrex Wafers

Endothelial cells and hepatocytes were also seeded onto etched silicon and pyrex wafers. Prior to cell seeding, the pyrex wafers were sterilized with 70% ethanol (Fisher) overnight and washed three times with sterile phosphate buffered saline (Gibco BRL). Silicon wafers were first soaked in acetone for 1 hr, followed a methanol rinse for 15 minutes, and overnight sterilization in 100% isopropyl alcohol. Onto these wafers were seeded rat lung microvascular endothelial cells at a density of $26.7 \times 10^3$ cells/cm$^2$, or rat hepatocytes at a density of $111.3 \times 10^3$ cells/cm$^2$. These cells were cultured at 5% $CO^2$ and 37° C., and their attachment and growth observed daily using microscopy.

Implantation of Hepatocyte Sheets into the Rat Omentum

Hepatocytes were cultured on silicon wafers coated with a thin layer of vitrogen (30 microgram/rill), and lifted in sheets. Retrorsine is a drug known to inhibit the regeneration of the normal liver by producing a block in the hepatocyte cell cycle with an accumulation of cells in late S and/or $G_2$ phase (Peterson J E J Pathol Bacterial 89, 153 (1965)). This drug was administered into the peritoneal cavity of two rats at a dose of 3 mg/ml/100 g on day 0, and after two weeks. Three weeks later, a portacaval shunt was created, and the following week a hepatocyte sheet, lifted after four days culture on vitrogen coated silicon (30 microgram/ml), was implanted onto the microvasculature of the rat omentum and rolled into a three-dimensional cylinder, and a 60% hepatectomy was performed. The rolled omentum with hepatocytes was harvested at four weeks and at three months after implantation and analyzed using histology.

Results

Micromachining

Figure 16A:
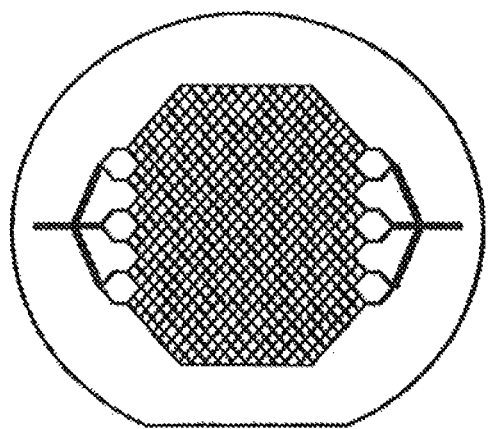
FIG. 16A shows a sample vascular branching network pattern used for silicon and pyrex wafer micromachining.
Figure 16B:
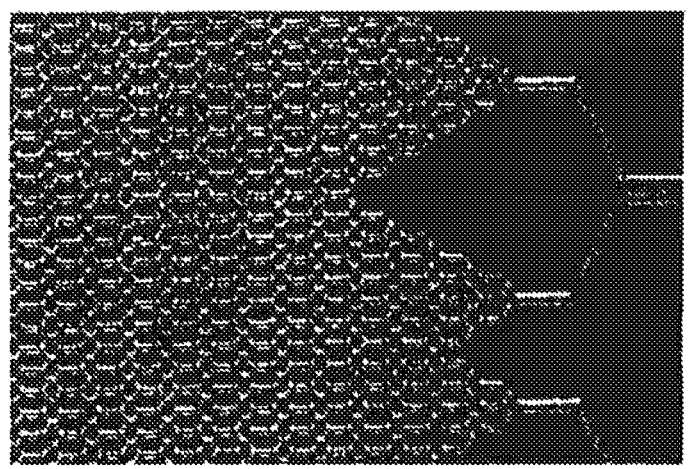
FIG. 16B shows the optical micrograph or portion of the capillary network etched into the silicon wafer using the process shown in FIG. 3.
Figure 16C:
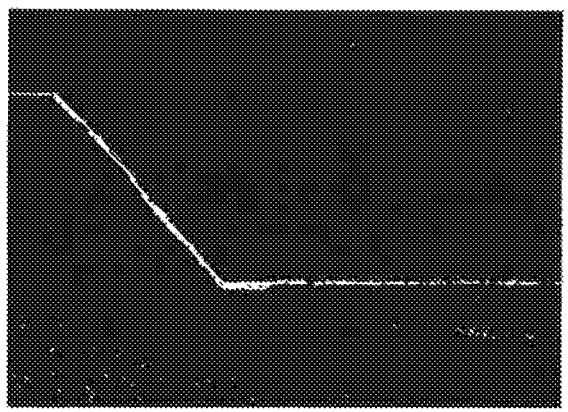
FIG. 16C shows a scanning electron micrograph of an anisotrophic etching process used to form angled sidewall trenches.

A schematic of the vascular branching network design used as a template for micromachining is shown in FIG. 16A. This pattern was transferred to silicon and pyrex wafers using the processes described in the Materials and Methods section. Typical trench depths of 20 μm on silicon and 10 μm on glass were achieved utilizing these processes. An optical micrograph of a portion of the capillary network etched into a silicon wafer is shown in FIG. 16B. In FIG. 16C, a Scanning Electron Micrograph cross-section of an angled trench etched using the anisotropic etching process described earlier is shown. This process resulted in excellent adhesion and enhanced lifting of living tissue.

Growth and Lifting of Cells from the Silicon and Pyrex Wafers

The adhesion and growth of endothelial cells and hepatocytes on several different substrate surfaces were compared. On all pyrex wafers, coated or non-coated, the endothelial cells proliferated and grew to confluence within four days. These cells did not lift spontaneously, and when scraped, did not lift as a single sheet. In addition, when the non-coated silicon wafers were seeded with endothelial cells, the cell sheet fragmented upon lifting. On the other hand, endothelial cells seeded onto silicon surfaces coated with vitrogen (30 microgram/ml), Matrigel (1%), and gelatin (10 mg/ml) did lift with the use of mechanical means (i.e. a cell scraper), and provided an intact monolayer sheet of endothelial cells. Upon observation, there were no significant differences in the effects of the three coatings on the detached cell sheets.

Hepatocytes also attached and spread well on all coated and non-coated pyrex wafers, and did not lift spontaneously or in sheets when scraped after several days of growth. However, when seeded onto silicon wafers, they lifted spontaneously on all the non-coated and coated wafers. The hepatocyte sheets lifted from the non-coated wafers after 3 days, but were very fragile and fragmented easily. The monolayers that lifted from the thin and thickly coated vitrogen substrates (30 microgram/ml and 3 microgram/ml) lifted after 4 days in culture to form an intact hepatocyte layer. Cells lifted from the Matrigel (1%) coated silicon wafers after 5 days in culture. There were no significant differences in appearance between the cell sheets lifted from the vitrogen and Matrigel coated wafers.

Histological assessment of the detached cell monolayers of both hepatocytes and endothelial cells manifested promising results. Hernotoxylin and Eosin (H&E) staining of both showed that all cells were viable and that most were undergoing mitoses. The endothelial cells were observed to be primarily attenuated and to form a single-celled alignment. The monolayer of hepatocytes showed each cell to be of a spheriod configuration with eosinophilic floculent cytoplasm and a large nucleus with a bright red nucleolus, similar to that seen in the native liver. Moreover, cellular attachments were less attenuated than the endothelial cells. Thus, these results are reminiscent of each of the cell types' specific functions. In biological systems, the endothelium functions to provide a thin, smooth outer surface of a barrier and a transport channel and so it is understandable that these cells are observed here to be primarily attenuated and in a single-celled array. The hepatocytes have more of a tendency to form tissue and so less of a single-celled array and more of a rounded multi-layered array is seen.

Albumin secretion into the hepatocyte culture medium at day 2, 3, 4, and 5 was 165.96 ±29.87, 164.44±17.22, 154.33±18.46, 115.47±18.09 (microgramiday, Graph 1), respectively. Though there was a statistically significant difference between day 4 and day 5, no significant differences were observed between day 2, day 3, and day 4 ($p<0.05$ by the paired t-test). Hence, this data shows that cells cultured on silicon wafers were able to maintain a fairly constant albumin production rate until day 4.

Moreover, through immunohistochemical staining of the detached hepatocyte monolayers, many cells were stained positive for albumin indicating further that hepatocyte function was maintained on silicon wafers.

Implantation of Hepatocyte Sheet into the Rat Omentum

H&E staining of hepatocyte sheets implanted into rat omentum demonstrated that all cells were viable and showed proliferation at four weeks and three months. The implanted hepatocyte monolayer sheets, when harvested, were over 5 cell layers thick in most areas. This study demonstrates that silicon microfabrication technology can be utilized to form large sheets of living tissue. It also demonstrates the feasibility of etching ordered branching arrays of channels that allow living endothelial cells to line the luminal surface of the channels. In addition, it has been shown that organized sheets of engineered hepatocyte tissue and endothelial tissue can be lifted from the surface of silicon or pyrex wafers and can be folded into a compact three-dimensional configuration. The hepatocyte sheets have then been placed into rats on the highly vascular surface of the omentum. That structure has then been rolled into a three-dimensional cylinder as a model for an engineered vasculature. Vascularized hepatic tissue was formed as a permanent graft.

EXAMPLE 2

Endothelialized Microvascular Networks Grown on Micromachined Pyrex® Templates for Tissue Engineering of Vital Organs This Example shows the design, modeling, and experimental/computational testing of the endothelialized microvascular matrices grown on micromachined Pyrex® templates.

Patterns of microvascular networks were etched using microfabrication technologies on Pyrex® wafers. The pattern consisted of 10 generations of bifurcations from a single inflow channel of width 3 mm down to channels of width of 30 μm.

The channels were then collected to a single outflow. All channels were etched to the same depth of 30 μm. The Pyrex® wafer was sealed to a flat silicone rubber sheet of the same size. Endothelial cells harvested from rat lung were successfully seeded and expanded under continuous flow conditions in this microvascular network. Red blood cells harvested from rat were heparinized and perfused into the endothelialized channels, and successfully collected at the output. Using micro-visualization techniques, the concentration of red blood cells (hematocrit) in the microvascular network was measured. The distribution of blood flow rate, pressure, and hematocrit was also calculated in the entire microvascular system using an earlier developed computational algorithm.

Epithelial cells were observed flowing through channels and attaching mainly around the walls of smallest channels on day 1 and growing to confluence along the channels under continuous flow conditions over the following 5 days. Rat lung endothelial cells attach in a single layer to the walls of these mold structures without occluding them.

Hematocrit compared well between the experimental measurements and numerical calculations. Red blood cells reach even the smallest vessels in the network, ensuring sustained transport of oxygen to the engineered capillaries.

In summary, microfabrication technology is demonstrated as an approach for organizing endothelial cells in vitro at the size scale of the microcirculation.

EXAMPLE 3

Microfluidics Device for Tissue Engineering Microvasculature: Endothelial Cell Culture In this Example, the fabrication of the microfluidic mold, in vitro seeding, and extended cell culture in the mold is demonstrated. Capillary networks were fabricated in biocompatible PDMS, sterilized, coated with cell adhesion molecules, and seeded with cells. Cell-containing molds were then connected to a closed-loop bioreactor for long-term culture. Continuous-flow culture of endothelial cells for up to 4 weeks without occlusion or contamination was achieved.

Traditional soft lithography microfluidics were used as a prototype matrix. These cell-containing microfluidics are capable of supporting long-term culture in vitro, because in vitro expansion of cells prior to implantation can take several weeks. The prototype matrix is designed to supply sufficient oxygen and nutrients and to remove excretory products while avoiding large shear stresses. The matrix is useful for long-term microfluidic cell culture, including the maintenance of sterility and the minimization of cell and bubble occlusions.

Microfluidic networks that support physiologic flows and pressures were developed by photopatterning SU-8, a high-aspect ratio negative photoresist, onto silicon. This was used as a mold for casting polydimethylsiloxane (PDMS). After removal from the mold, inlets and outlets were cored with blunted syringe needles, and the micropatterned polymer scaffold was irreversibly sealed to an unpatterned layer of Pyrex® or PDMS by oxygen plasma surface treatment. See Duffy, et al., Anal. Chem. 70, 4974 (1998). The microfluidic device was autoclave sterilized and perfused with a solution containing cell adhesion molecules (poly-L-lysine, collagen, gelatin, or fibronectin), which were allowed to adsorb for one hour.

The fluidic network was then seeded with a $1 \times 10^6$-$1 \times 10^8$ cells/mL cell suspension using a syringe pump at flow rates ranging from 10-100 μL/min. The cells were then allowed to attach for 24 hours, after which the device was connected in-line with a sterile bioreactor consisting of a peristaltic pump, oxygenator, bubble trap, and a reservoir of sterile culture medium. Sterile culture medium was pumped peristaltically from a sterile reservoir through an oxygenator consisting of along length of tubing semipermeable to oxygen. The oxygenator was followed by a small bubble trap, leading directly to the microfluidic circuit. Finally, the system was run closed-loop in an incubator at standard culture settings.

Autoclave sterilization of the microfluidic circuit caused no obvious pattern distortion. Coating the channels with cell adhesion molecules enhanced cell attachment when compared to phosphate buffered saline-coated control channels. Seeding of cells into channels of widths between 30-200 μm was optimized by varying concentrations and flow rates. The continuous-flow bioreactor was used to dynamically culture endothelial cells at flow rates between 0.01 mL/min and 0.1 mL/min. Both single channels and complex networks of channels (30-200 μm wide and 40 μm deep) were successfully seeded and cultured. In 100 μm×40 μm single channels, cells were cultured for more than 4 weeks without contamination or occlusion.

Long term culture of cells in microfluidic devices was achieved. Cells successfully attached, proliferated, and migrated in closed microfabricated channels with small geometries.

EXAMPLE 4

Generation of Functionally Differentiated, Three-Dimensional Hepatic Tissue from Two-Dimensional Sheets of Small Hepatocytes and Non-Parenchymal Cells In this Example, three-dimensional, vascularized liver tissue was fabricated in vivo from a non-vascularized monolayer or cell sheet of small hepatocytes (SHCs) formed on a silicon wafer. SHCs cells are smaller than mature hepatocytes (MHCs), but morphologically similar, with a highly proliferative capacity (Mitaka, et al., Biochem Biophys Res Commun 214, 310 (1995); Mitaka, et al., Gastroenterol Ilepatol 13 Suppl, S70 (1998); Mitaka, et al., Hepatologoy, 29, 111 (1999); Tateno, et al., Am J Pathol 148, 383 (1996); Tateno, et al., Am J Pathol 149, 1593 (1996)).

Cell sheets created from SHCs and NPCs were implanted onto rat omentum with maximal hepatotrophic stimulation by retrorsine, portacaval shunt, and partial hepatectomy, and their engraftment and function were evaluated. Using this cell type, co-cultured with nonparenchymal cells (NPCs), liver tissue that maintained a high level of albumin production was fabricated in a flow culture system. Animals as described in Example 1 were used as cell donors. Cells were cultured as described in the Hepatocyte Culture Medium section of Example 1.

Cell Isolation

SHCs and NPCs were isolated by the process described in Example 1, with the following modifications. Animals were anesthetized by an intramuscular injection with Ketamine and Xylazine. Cells were collected, suspended, filtered and centrifuged as previously described. Following centrifugation, the pellet containing a majority of MHCs was discarded. The supernatant was collected, and the fraction containing SHCs and NPCs was obtained as a pellet by additional centrifugation twice at 150×g for 5 minutes. The pellet was resuspended in the plating medium and the cell number and viability were counted using the trypan blue exclusion test.

In Vitro SHC Sheets Preparation

In order to obtain SHC sheets, the SHCs and NPCs were seeded and cultured on silicon wafers (10 cm diameter). Briefly, the silicon wafers were sterilized with ethylene oxide gas and coated with liquid collagen (Vitrogen 100, Collagen Corp., Palo Alto, Calif.). The mixture of SHCs and NPCs was resuspended in the plating medium at a density of $0.8 \times 10^6$ cells/mL. A 25 mL suspension was seeded onto the silicon wafer in a 15 cm Petri dish and incubated at 37° C., 5% $CO_2$. The plating medium was changed every other day. After reaching confluence, the cultured cells were lifted as sheet by scraping with a sterile razor blade and prepared for implantation.

Albumin Production

To assess SEC function before implantation, albumin concentration in the plating medium was measured at 3, 5, 7 and 10 days after cell seeding using an enzyme linked immunosorbent assay (ELISA) (n=11) as described in Example 1.

In Vivo Model

Retrorsine was administered into the peritoneal cavity of recipient rats (n=23) at a dose of 3 mg/ml/100 g on day 0, and after two weeks as previously reported (Laconi, et al., Am J. Pathol 153, 319 (1998)). Three weeks after the second administration, an end-to-side portacaval shunt was created using 8-0 Ethilon suture (ETHICON, Somerville, N.J.) to generate systemic hepatoirophic stimulation for SHC sheet implantation. One week later, a SHC sheet was spread onto the rat omentum and rolled from distal to proximal into a three-dimensional cylinder. The omentum was sutured to the anterior wall of the stomach using 7-0 Prolene suture (ETHICON). A 60% partial hepatectomy was performed simultaneously for hepatotrophic stimulation. Animals were sacrificed at the designated time points after SHC sheet implantation for specimen retrieval. The resected specimens were fixed in 10% formalin solution (Sigma), routinely processed and embedded in paraffin for subsequent hematoxylin-eosin (H & E) and immunohistochemical staining. Two specimens were fixed in 2.5% gluteraldehyde (Sigma) for electron microscopy (EM).

Immunohistochemical Staining

To characterize the implanted constructs, immunohistochemical staining using the Avidin-biotin peroxidase complex (ABC) method was performed. The primary antibodies included: rabbit anti-albumin (DAKO, Carpinteria, Calif.), rabbit anti-transferrin (ICN), mouse anti-pancytokeratin (Sigma), goat anti-γ-glutamyl transpeptidase (OTT) (a gift from Dr. Petersen, Department of Pathology, University of Florida, Fla.). Four .mu.m paraffin sections were deparaffinized and treated with 4.5% $H_2O_2$ in methanol. The specimens were digested for 12 minutes with 0.1% trypsin solution, followed by treatment with avidin D (Vector) and 5% serum. Subsequently, slides were incubated with the respective primary antibody that were diluted in phosphate buffered saline with 1% bovine serum albumin overnight at 4° C. Biotinylated antimouse/rabbit/goat antibody was used as a secondary antibody in combination with the Vectastain ABC kit (Vector, Burlingame, Calif.). Finally, specimens were treated with 3-amino-9-ethylcarbazole (AEC) (Vector) as substrate and were counterstained with. Mayer's hematoxylin solution (Sigma).

Electron Microscopy (EM)

Two rats at 4 months were sacrificed for EM study. Immediately after removal from the animal, 1 mm sections were placed into Karnovsky's KII solution (2.5% glutaraldehyde, 2.0% paraformaldehyde, 0.025% calcium chloride, in a 0.1 M sodium cacodylate buffer, pH 7.4), fixed overnight at 4° C., and routinely processed for EM. Representative areas were chosen from 1 μm sections stained with toluidine blue. The sections were examined using a Phillips 301 transmission electron microscope.

Morphologic and Quantitative Analysis

For morphologic and quantitative analysis, specimens were harvested at 2 weeks (n=7), 1 month (n=7), and 2 months (n=7). At each time point, the rolled omentum was cut perpendicularly to the greater curvature of stomach, and three to four cross-sections of tissue were obtained and stained with H & E. The area occupied by implanted constructs in each section was measured using computer assisted analysis with NIH Image version 1.61 software (Division of Computer Research and Technology, NIH, Bethesda, Md., USA). This was expressed as $\mu m^2$/section.

Statistical Analysis

All values are expressed as mean f SD and were statistically evaluated using the Mann-Whitney test or the paired t-test. A value of $p<0.05$ was considered statistically significant.

Cell Isolation and Growth in a Culture Flask

Figure 17A:
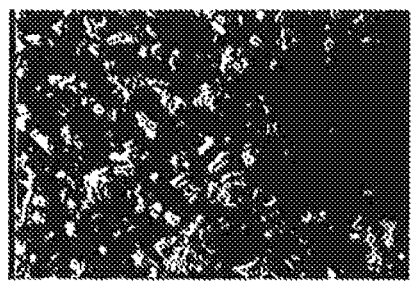
FIGS. 17A-C show phase-contrast photographs of small hepatocytes and nonparenchymal cells cultured on regular culture flasks.
Figure 17B:
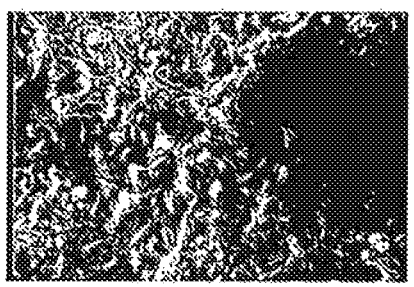
Figure 17C:

All cell isolations yielded $8-14 \times 10^7$ cells comprising SHCs and NPCs with >90% overall viability. To evaluate the culture condition of SHCs on silicon wafers, a cell suspension was seeded on culture flasks at the same concentration. One day after seeding, most cells began to attach individually or occasionally form small clusters consisting of several SHCs. After 3 days, cells have completely attached and spread on the culture flask. After 5 days, many clusters had formed and NPCs were observed between the clusters. These small clusters united to form larger clusters and continued to grow until implantation (FIG. 17).

Cell Sheet Formation

Figure 18A:
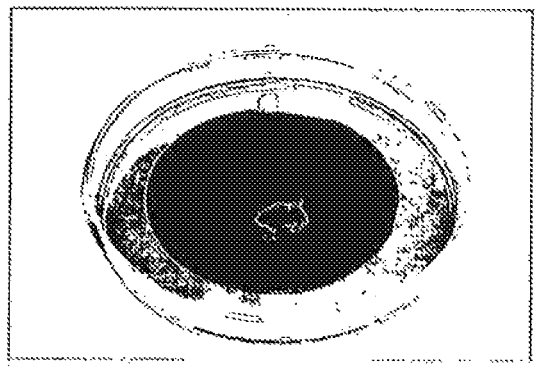
FIGS. 18A and 18B show a cell sheet lifted from a silicon wafer.
Figure 18B:
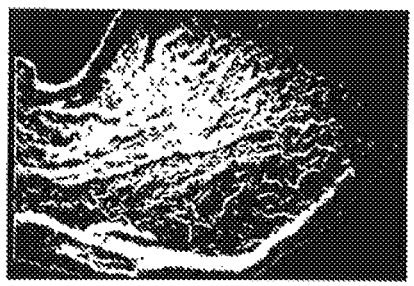

SHCs and NPCs cultured on silicon wafers grew similarly to the culture flask. Many large clusters were observed macroscopically on the silicon wafers after culturing for 10-14 days. Cultured cells were lifted as a sheet from all the silicon wafers. After lifting, cell sheets shrunk to approximately 2.5 cm in diameter (FIG. 18)

Albumin Production

Figure 19:
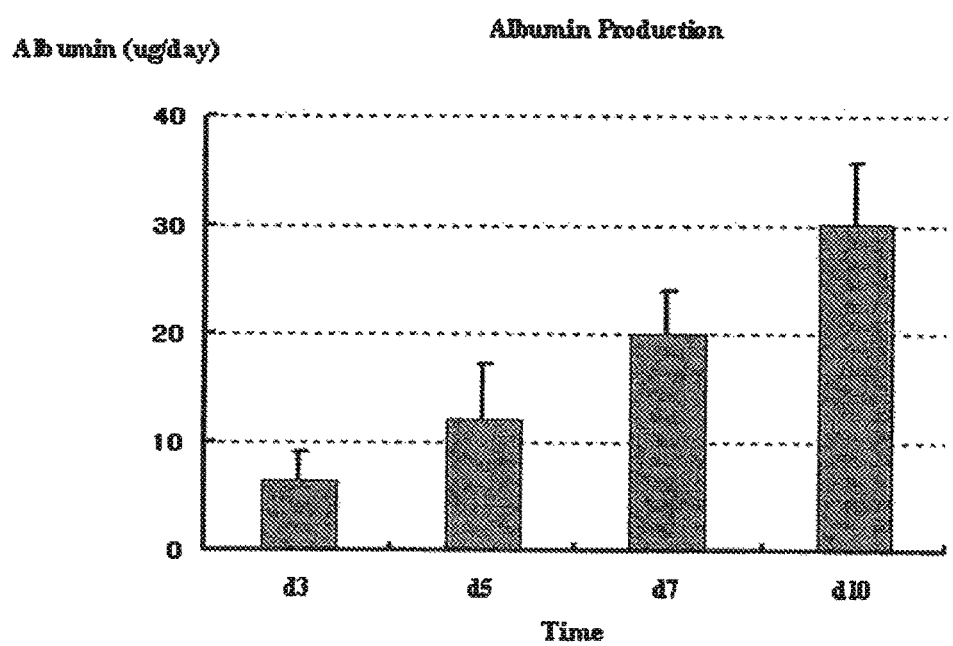
FIG. 19 shows albumin production by small hepatocytes at day 3, 5, 7, and 10 (μg/day).

Albumin secretion at day 3, 5, 7, and 10 was, 6.47±2.49, 12.08±5.18, 19.93±4.05, 30.14±5.46 (au/day), respectively (FIG. 19). There were statistically significant differences between day 3 and day 5, day 5 and day 7, and day 7 and day 10 ($p<0.05$ by the paired t-test).

H & E Staining

Figure 20A:
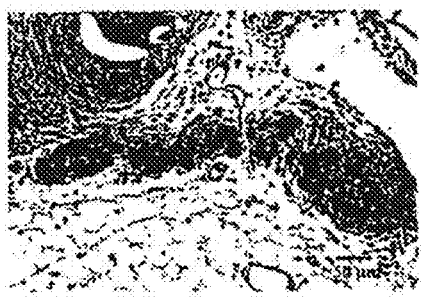
FIGS. 20A-D show H & E staining of implanted constructs.
Figure 20B:
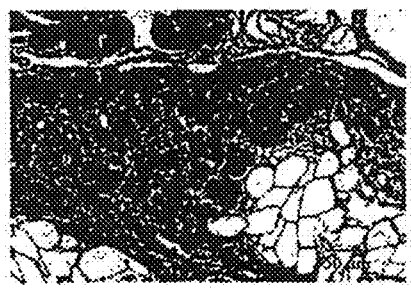
Figure 20C:
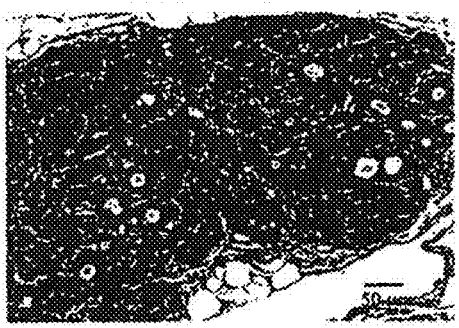
Figure 20D:

The H & E staining of specimens harvested at 2 weeks after cell sheet implantation typically reveal large, polygonal, eosinophilic cells with round nuclei resembling hepatocytes, cuboidal cells resembling biliary epithelial cells, and capillary formation. At this time point the area of hepatocytes was less than five cell layers thick (FIG. 20A). At 1 and 2 months, large clusters of hepatocytes over five cell layers thick, cuboidal cells resembling biliary epithelial cells, and capillary formation could be observed (FIGS. 20B-D). In some areas, hepatocytes exceeded ten cells layer thick. In the specimens at 2 weeks and 1 month, there were many areas that were occupied mainly by bile duct-like structures (FIG. 20D). As the implant matured in the omentum, the number of hepatocytes increased and the number of bile duct-like structures decreased at 2 months.

Immunohistochemistry

Figure 21A:
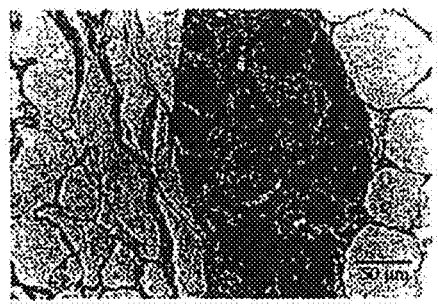
FIGS. 21A-D show immunohistochemical staining of implanted constructs.
Figure 21B:
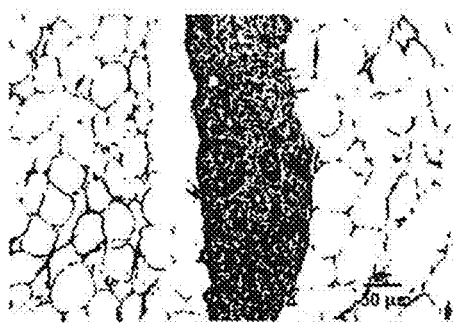
Figure 21C:
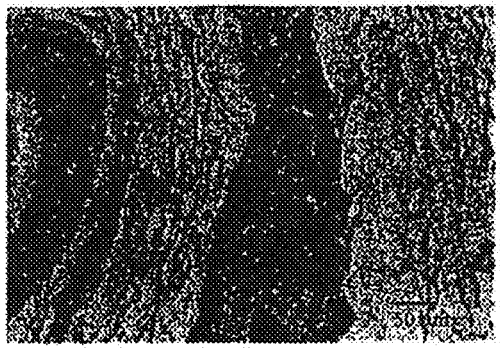
Figure 21D:
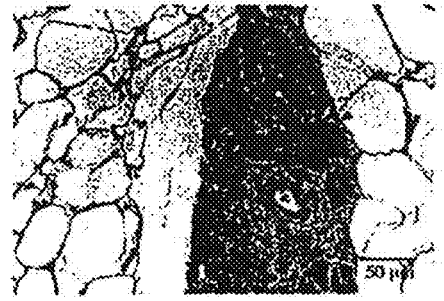

Both hepatocytes and bile duct-like structures stained positively with pan-cytokeratin. However, bile ductules stained more strongly positive than hepatocytes (FIG. 21A). Since there are normally no pan-cytokeratin positive cells in the omentum, it is likely that the cells originated from the implanted constructs. Some of the hepatocytes stained positively for albumin and transferrin, which suggests that they continued to express liver specific functions. The bile duct-like structures stained positively for GGT, an enzyme expressed at high levels in normal rat intrahepatic biliary epithelial cells but typically not detected in normal rat hepatoeytes, and negatively for albumin and transferrin, which indicated that they were composed of cells resembling normal biliary epithelial cells (FIGS. 21B-D).

Figure 22:
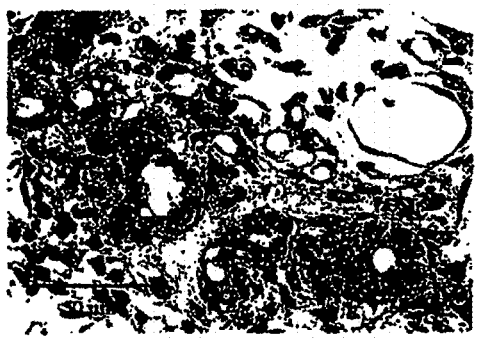
FIG. 22 shows H & E staining at 1 month. Arrow indicates the bile ductular structure composed of both biliary epithelial cells and a hepatocyte. Arrow heads indicate the bile ductular structures composed of biliary epithelial cells.

In one case, histology showed that one bile duct-like structure at 2 weeks was formed with both cells resembling biliary epithelial and cells which were morphologically more similar to hepatocytes (FIG. 22). This bile duct-like structure was located between the canaliculi-like structures composed of hepatocytes, and the bile duct-like structures formed solely by cells resembling biliary epithelial as if it were a transitional structure between the two. This phenomenon demonstrates that canaliculi-like structures and bile duet-like structures grow to confluence in tissue engineered constructs.

Ultrastructure of the Implanted Construct

Figure 23A:
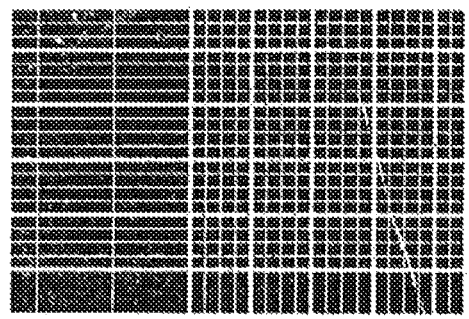
FIGS. 23A-B show transmission electron microscopy (TEM) of an implanted construct.
Figure 23B:
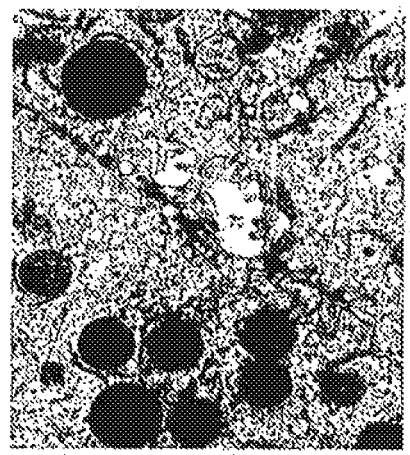

TEM revealed that the engineered constructs were composed of cells with large round nuclei, numerous mitochondria and peroxisomes, and microvilli; characteristic of hepatocytes. These cells formed structures resembling bile canaliculi at the cell-cell borders. Capillaries were seen between hepatocytes (FIG. 23B).

Morphologic and Quantitative Analysis

Figure 24:
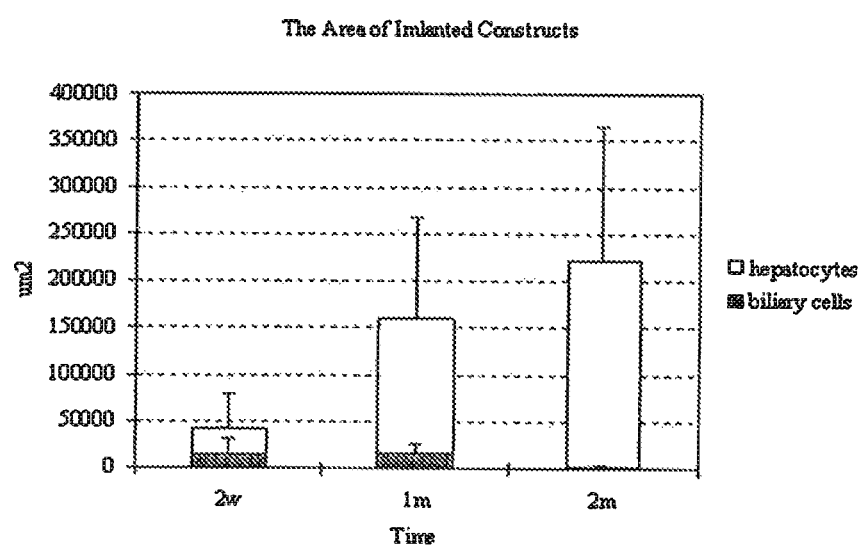
FIG. 24 shows the area occupied by implanted constructs (μg$^2$/section). Total area and bile ducts area are expressed as mean+/−SD.
Figure 25:
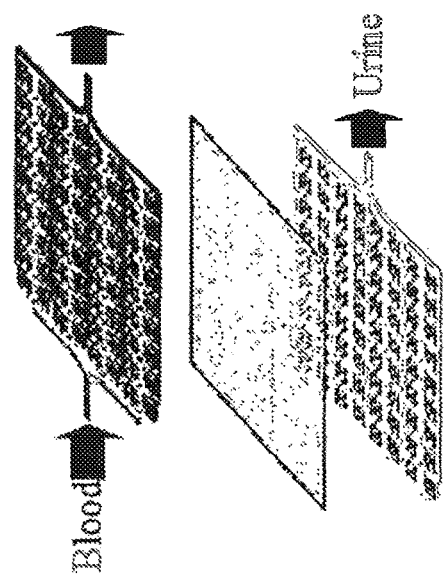
FIG. 25 shows a schematic diagram of a micromachined apparatus for tissue engineered renal replacement. The apparatus comprises a compartment with a glomerular endothelial filter for circulatory flow (42), a semi-permeable membrane for mass transfer of oxygen, nutrients and waste (44), and a compartment with a proximal tubule network excretory system, which includes inlets for filtration of urine (46).
Figure 26:
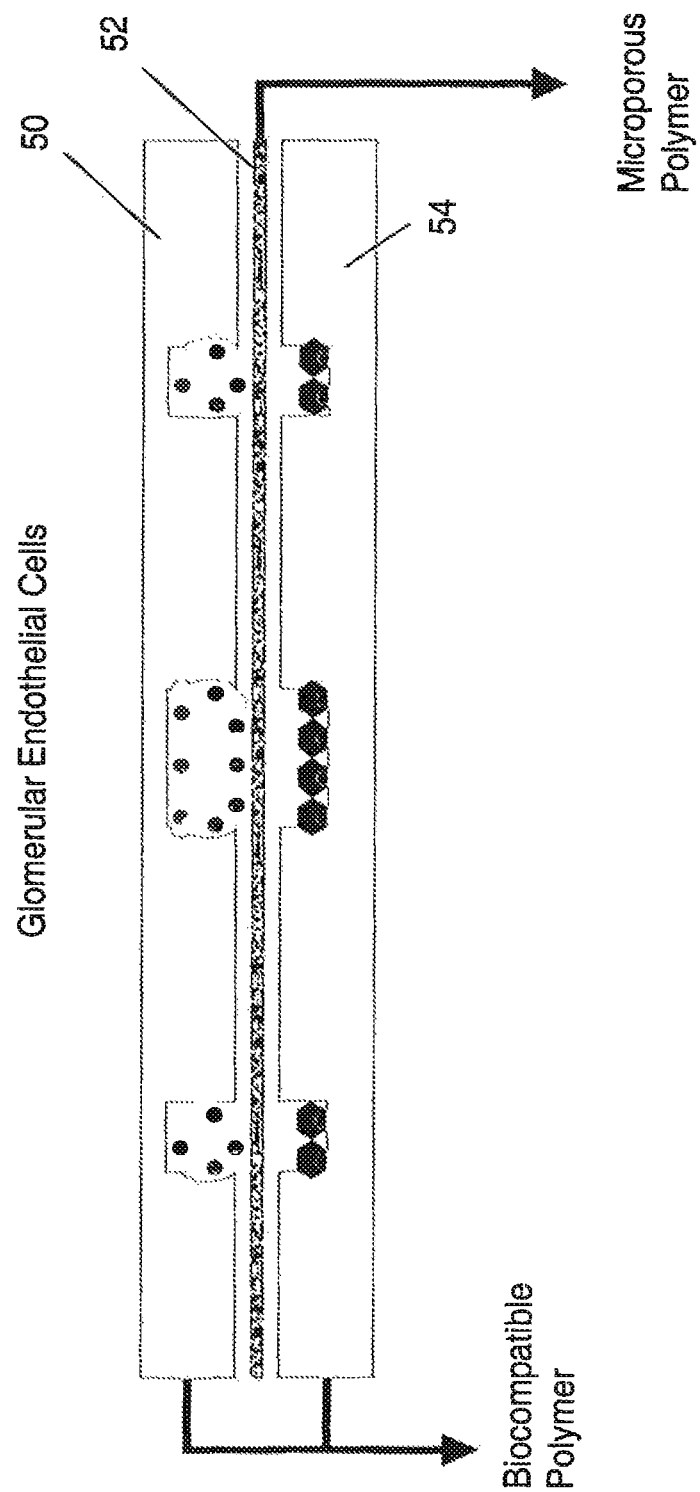
FIG. 26 shows a cross section of a micromachined apparatus for tissue engineered renal replacement. The apparatus comprises a compartment with a glomerular endothelial filter for circulatory flow, a semi-permeable membrane for mass transfer of oxygen, nutrients and waste, and a compartment with a proximal tubule network excretory system, which includes inlets for filtration of urine. Each compartmentalized layer of the apparatus comprises a biocompatible polymer and the layers are separated by a semi-permeable membrane comprising a microporous polymer.
Figure 27:
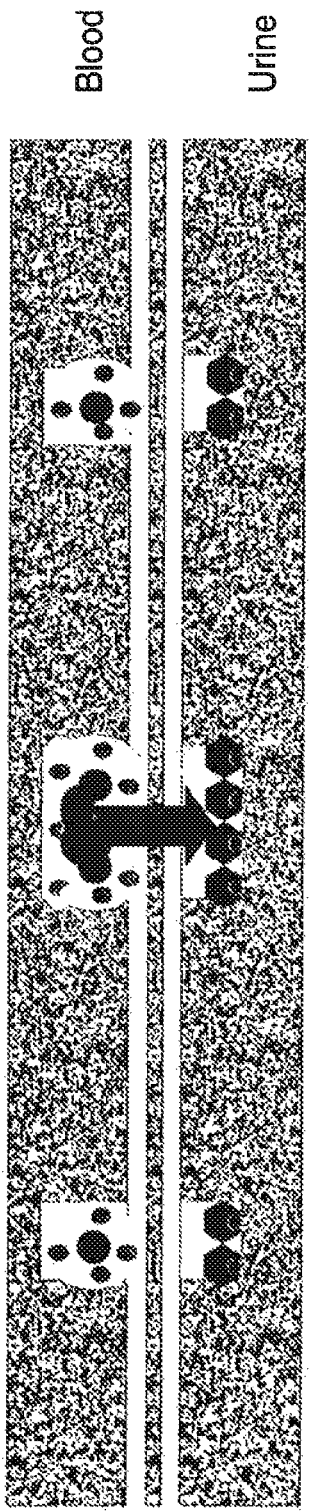
FIG. 27 shows a cross section of a micromachined apparatus for tissue engineered renal replacement. The direction of flow of glomerular ultrafiltrate is shown. Flow originates in the layer comprising glomerular endothelium, passes through the semi-permeable membrane to layer comprising the proximal tubule network where reabsorption occurs.

The calculated areas occupying implanted constructs were 43136+/−36181, 153810+/−06422, and 224332+/−142143 $\mu m^2$/section at 2 weeks, 1 month, and 2 months, respectively. The mean area increased over time, and there were significant differences between 2 w and 1 m ($p<0.05$), and between 2 w and 2 m ($p<0.01$). No significant difference was observed between 1 m and 2 m. The areas occupied by bile duct-like structures were 13407+/−16984, 15430+/−8980, and 1290+/−2052 $\mu m^2$/section at 2 weeks, 1 month, and 2 months, respectively. The areas were significantly greater at 2 weeks ($p<0.01$) and 1 month ($p<0.05$ by the Mann-Whitney U test), compared to the area at 2 months (FIG. 24).

This Example shows morphologically simple cell sheets created from SHCs and NPCs implanted and engrafted in the omentum. Given adequate hepatotrophic stimulation, implants formed morphologically complex three-dimensional tissue consisting of hepatocytes, structures resembling bile canaliculi, and ducts composed of cells resembling biliary epithelium. These results represent a significant advance toward the tissue engineering of complex vascularized thick tissues.

EXAMPLE 5

Generation of a Renal Replacement Device

This Example describes a microfabricated network of proximal tubules that could potentially replace the essential reabsorptive and excretory functions of the kidney. (See FIGS. 25-28.) A glomerular endothelial cell-lined network can provide filtration while minimizing thrombosis. These two networks combined on bioresorbable polymer are the basis far a tissue engineered renal replacement device.

Background

Although the kidney is a complex organ with an intricate vascular supply and at least 15 different cell types, the critical functions of filtration, reabsorption and excretion can be targeted with tissue engineering. The basic functional unit of the kidney, the nephron, is composed of a vascular filter, the glomerulus, and a resorptive unit, the tubule. Filtration is dependent on flow and specialized glomerular endothelial cells. The majority (50-65%) of reabsorption is performed by the proximal tubule cells using active sodium transport through the energy-dependent $Na^+$-$K^+$-ATPase located on the basolateral membrane. Only 5-10% of the approximately one million nephrons in each human kidney is required to sustain normal excretory function.

Figure 28:
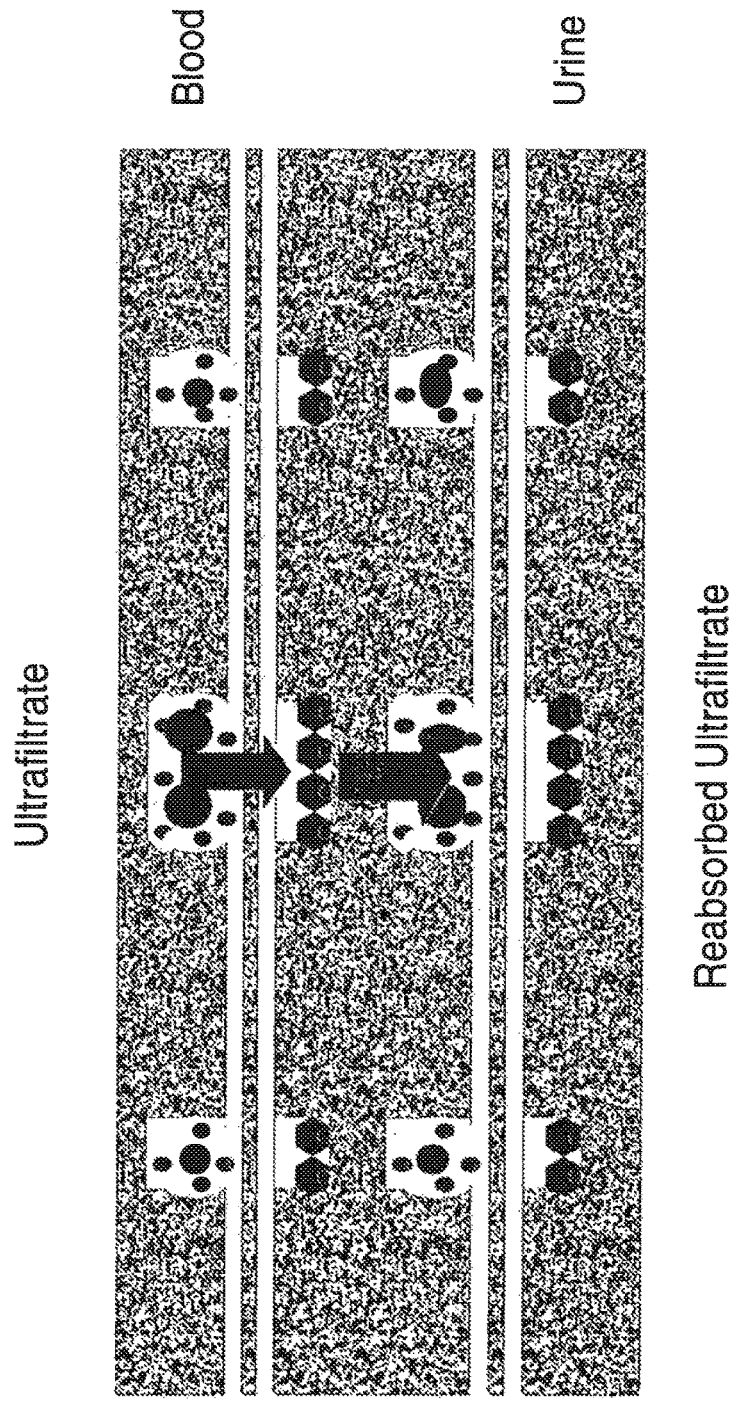
FIG. 28 shows a cross section of a micromachined apparatus for tissue engineered renal replacement comprising multiple stacked layers. The apparatus comprises repeating, stacked units, each unit comprising a compartment with a glomerular endothelial filter for circulatory flow, a semi-permeable membrane for mass transfer of oxygen, nutrients and waste, and a compartment with a proximal tubule network excretory system, which includes inlets for filtration of urine.

The design of a tissue engineered renal replacement device can then be focused an the development of a glomerular endothelial filter in conjunction with a proximal tubule device for reabsorption and excretion. The endothelial filter is specifically designed to provide physiologic flow with low thrombogenicity and maximized surface area for solute transport. The proximal tubule device, containing an appropriate number of cells for renal replacement, has optimized surface area for solute reabsorption and an outlet for urine excretion. (See FIG. 27.) Several layers of molds and/or polymer scaffolds and semi-permeable membranes can be stacked to optimize filtration and reabsorption (FIG. 28). Biocompatible, bioresorbable and microporous polymers are used throughout for optimal cell growth and function.

Materials and Methods

Configuring the Mold

MEMS replica molding was used to create the polymer molds used in this Example (FIG. 2). Using the techniques described herein, an inverse pattern (i.e., protrusions rather than indentations) corresponding to the desired pattern of microchannels was formed on a silicon wafer. Poly-(dimethyl siloxane) (PDMS) was then cast onto the silicon template. After the template was removed, the PDMS was subjected to $O_2$ plasma treatment, and was fastened to a second layer of PDMS. In this Example, the second layer of PDMS was flat, however, in other embodiments, either or both surfaces of the second PDMS layer can contain a pattern of microchannels. In addition, a semi-permeable membrane can be fastened between the PDMS layers.

Cell Culture

Renal proximal tubule cells and glomerular endothelial cells from rat and pig models have been isolated using sieve filtration and separation over a Percoll gradient (Vinay, et al. Am J Physiol 241, F403 (1981); Misra, et al. Am J Clin Path 58, 135 (1972)). Human microvascular endothelial cells were isolated from normal neonatal foreskin in collaboration with Dr. Michael Detmar (Cutaneous Biology Research Center, MGH Charletown), and stained positively for endothelial cell markers CD-31 and von Willebrand's factor (vWF) within the PDMS devices.

Both renal proximal tubule cells and human microvascular endothelial cells were seeded into the MEMS-designed PDMS (poly(dimethyl siloxane)) devices at 20 million cells/ml. Cells were allowed to adhere at 37° C. for six hours. Devices were rotated 180° degrees at three hours to allow adherence of cells to both side's of the microchannels. Flow was then started via infusion pump with appropriate culture medium to maintain cell viability.

Animal Model

The appropriate animal is made uremic via bilateral nephrectomies and connected to a hemoperfusion circuit, The tissue engineered renal replacement device is connected such that the venous blood enters the glomerular endothelial network and is returned to the animal. The fluid filtered through the glomerular network then passes through the proximal tubule network. Reabsorbed fluid is returned to the animal, while the fluid remaining in the proximal tubule lumen is analyzed as processed ultrafiltrate (urine). The goal rate of hemofiltration is 15-20 ml/min. to match the rate used in renal dialysis. Function of the renal replacement device is assessed as compared to matched controls for electrolytes, blood urea nitrogen and creatinine levels, glutathione reabsorption, ammonia excretion, and 1,25-(OH), $D_3$ levels.

Results

Figure 29:
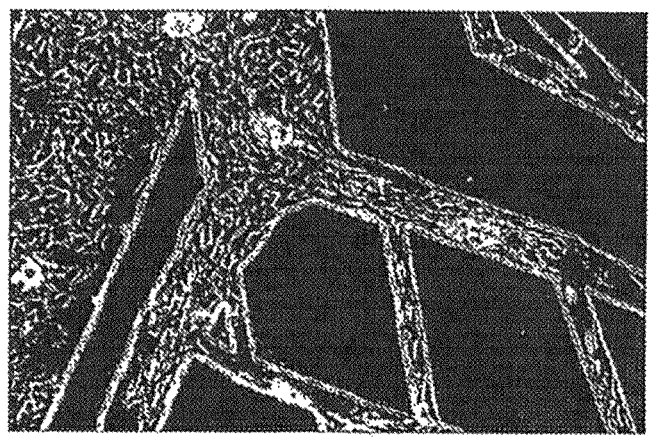
FIG. 29 shows human microvascular cells at 14 days after seeding in microchannels.

Human microvascular endothelial cells were seeded into poly (dimethyl siloxane) (PDMS) microchannels (smallest channel width 30 depth 35 µm) using the specifically designed MEMS templates, and good cell adherence and proliferation within the channels was observed (FIG. 29).

A computational model is used to maximize blood flow through the glomerular cell filter, within normal hernodynamic parameters. Finite Element Modeling (FEM) technologies are used to maximize the surface area for filtration to simulate mass transport of solutes across the filter. The template topography and branching angles are designed to minimize thrombosis within the microchannels. Similarly, the proximal tubule network is optimized to provide even flow distribution, surface area for reabsorption, and an outflow tract for excretion of urine.

Cultured proximal tubular cells exhibit characteristic dome formation. Glomerular endothelial cells have also been isolated and maintained in culture. Further characterization of the cells is performed using immunohistochemical staining. Proximal tubule cells are stained for megalin (gp330) expression, and endothelial cells are stained for von Willebrand's factor (vWF) and CD-31.

Function of proximal tubule cells is assessed with the conversion of 1,25-OH-$D_3$ to 1,25-$(OH)_2D_3$ (1,25-dihydroxyvitamin $D_3$), the reclamation of glutathione and the generation of ammonium using a single pass perfusion system. 25-(OH) D3-12-hydroxylase is a cytochrome P-450 monooxygenase found in the inner mitochondrial membrane of proximal tubule cells. Proximal tubule glutathione reclamation is performed by the brush-border enzyme gamma-glutamyl transpeptidase. In addition, specific transport functions such as vectoral fluid transport (inhibited by ouabain, an $Na^+$-$K^+$-ATPase inhibitor), active bicarbonate and glucose transport (inhibited by acetazolamide and phlorizin respectively), and para-aminohippurate secretion (inhibited by probenecid) are also tested (Humes, et al., Kid Int 55, 2502 (1999); Humes, et al. Nat Biotechnol 17, 451 (1999)). Glomerular endothelial cell function is assessed for permeability to water and serum proteins, and the basement membrane components analyzed.

Figure 30:
FIG. 30 shows proximal tubule cells growing in a poly dimethyl-siloxane (PDMS) polymer scaffold at approximately 5 hours after seeding.
Figure 31:
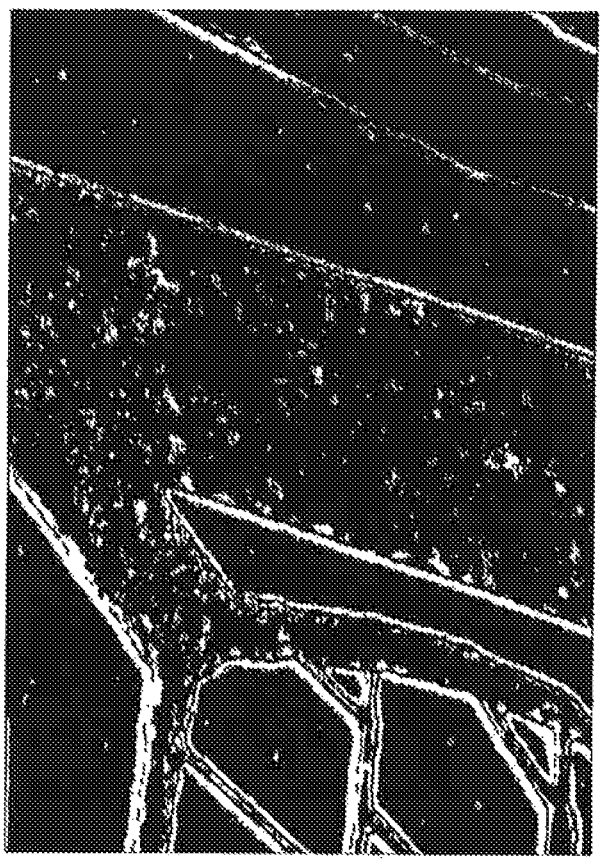
FIG. 31 shows proximal tubule cells growing in a poly dimethyl-siloxane (PDMS) polymer scaffold at 2 days after seeding.
Figure 32:
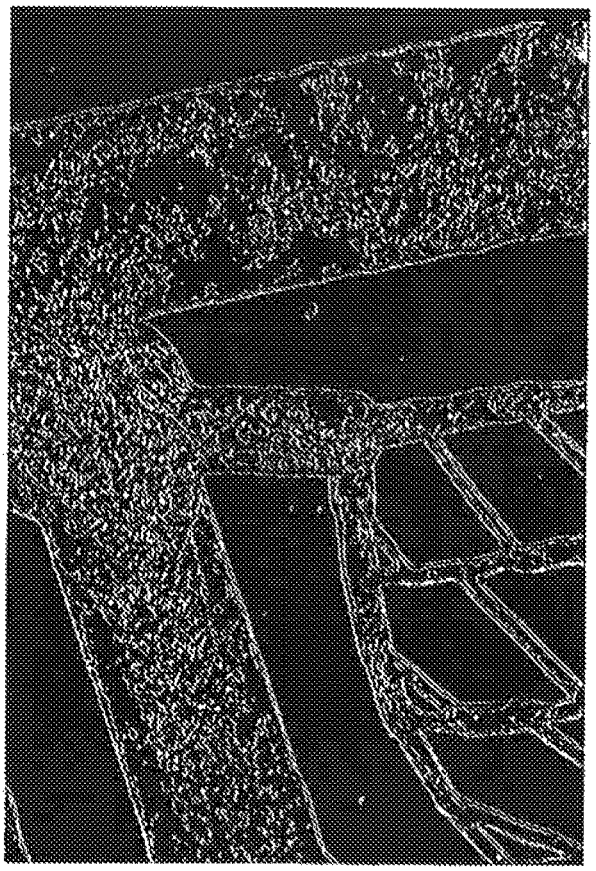
FIG. 32 shows proximal tubule cells growing in a poly dimethyl-siloxane (PDMS) polymer scaffold at 6 days after seeding.

Microvascular endothelial and proximal tubule cells into have been successfully seeded into PDMS networks made from MEMS templates. FIGS. 30-32 show proximal tubule cells growing in the microchannels of the polymer scaffold at various intervals after seeding.

After generation of microporous biodegradable polymer templates, specific cell attachment and proliferation are tested using DNA or MIT assays. Cells on polymer templates are examined for confluence using histology and electron microscopy, as well as insulin leak rates (<10% infused). Enhanced attachment of proximal tubule and glomerular endothelial cells to polymers is optimized by precoating the polymer surface with several extracellular matrix components (Matrigel, collagen, fibronectin and laminin) or peptide sequences such as RGD, as described herein.

Flow studies are performed in glomerular endothelial and proximal tubule networks in vitro to simulate physiologic blood flow and hemodynamic parameters and to examine cell viability and function.

Having thus described in detail preferred embodiments of the present invention, it is to be understood that the invention defined by the appended claims is not to be limited to particular details set forth in the above description, as many apparent variations thereof are possible without departing from the spirit or scope of the present invention. Modifications and variations of the method and apparatuses described herein will be obvious to those skilled in the art, and are intended to be encompassed by the following claims.

We claim:

1. A lamina assembly comprising:
   a lower structure having an upper side defining lower structure channels;
   an upper structure having a lower side defining at least one upper structure microchannel that opposes the lower structure channels;
   a semi-permeable membrane disposed between the lower and upper structures to separate the respective channels; and
   cells cultured on at least one side of the semi-permeable membrane.

2. A lamina assembly as recited in claim 1, wherein the lower and upper structures are fastened together.

3. A lamina assembly as recited in claim 1, wherein each of the first and second structures and the semi-permeable membrane are comprised of material that is suitable for attachment and culturing of animal cells and the cells are animal cells.

4. A lamina assembly as recited in claim 1, wherein the cells are cultured on both sides of the semi-permeable membrane.

5. A lamina assembly as recited in claim 1, wherein the lower structure channels form an inlet in fluid communication with an outlet through a plurality of branching channels.

6. A lamina assembly as recited in claim 5, further comprising a nutrient supply connected to the inlet and an excretion removal line connected to the outlet.

7. A lamina assembly as recited in claim 5, further comprising a pump connected to the inlet for circulating fluid through the tissue lamina assembly.

8. A lamina assembly as recited in claim 5, wherein the inlet is directly connected to blood vessels of an animal.

9. A lamina assembly as recited in claim 1, wherein in the upper structure at least one microchannel forms a branching pattern identical to a branching pattern in the lower structure.

10. A lamina assembly as recited in claim 1, wherein the upper structure has an upper side defining upper structure channels, and
    further comprising: a second upper structure having a lower side defining second upper structure channels that oppose the upper structure channels of the upper side; and a second semi-permeable membrane disposed between the upper and second upper structures to separate the respective channels; and
    cells cultured on at least one side of the second semi-permeable membrane.

11. A lamina assembly as recited in claim 10, wherein the second upper structure has an upper side defining second upper structure channels, and
    further comprising: a third upper structure having a lower side defining third upper structure channels that oppose the second upper structure channels of the upper side; and a third semi-permeable membrane disposed between the second and third upper structures to separate the respective channels; and
    cells cultured on at least one side of the third semi-permeable membrane.

12. A lamina assembly as recited in claim 1, wherein the lower structure channels are open-faced channels and open portions of the lower structure channels are adjacent to the semi-permeable membrane.

13. A lamina assembly as recited in claim 1, further comprising a second tissue lamina assembly attached to the upper structure, the second tissue lamina assembly including: a third structure having a side defining third structure channels; a fourth structure having a side defining fourth structure channels that oppose the third structure channels; a second semi-permeable membrane disposed between the third and fourth structures to separate the respective channels; and cells cultured on at least one side of the semi-permeable membrane.

14. A lamina assembly for supplementing or replacing at least one organ function, comprising:
    a lower structure having an upper side defining a plurality of lower microchannels;
    an upper structure having a lower side defining at least one channel that opposes at least a portion of the lower microchannels;
    a semi-permeable membrane disposed between the lower microchannels and the at least one channel; and
    cells cultured on at least one of the semi-permeable membrane, the lower structure or the upper structure.

15. A lamina assembly as recited in claim 14, wherein the plurality of lower microchannels have endothelial cells seeded therein and the at least one channel has parenchymal cells therein.

16. A lamina assembly as recited in claim 14, wherein the semi-permeable membrane allows exchange of oxygen, nutrients and waste between fluid circulating in the plurality of lower microchannels and the at least one channel.

17. A lamina assembly as recited in claim 14, wherein each of the lower and upper structures and the semi-permeable membrane are comprised of material that is suitable for attachment and culturing of animals cells, and wherein animal cells are cultured on both sides of the semi-permeable membrane.

18. A lamina assembly as recited in claim 14, wherein the lower and upper structures are fastened together and the plurality of lower microchannels form at least one inlet in communication with at least one outlet.

19. A lamina assembly as recited in claim 14, further comprising cells cultured on at least one side of the semi-permeable membrane, wherein the plurality of lower microchannels are branched microchannels.

* * * * *